US010918628B2

(12) United States Patent
Höglinger et al.

(10) Patent No.: US 10,918,628 B2
(45) Date of Patent: Feb. 16, 2021

(54) TREATMENT OF SYNUCLEINOPATHIES

(71) Applicants: Deutsches Zentrum für Neurodegenerative Erkrankungen e. V. (DZNE), Bonn (DE); Klinikum rechts der Isar der Technischen Universität München, Munich (DE)

(72) Inventors: Günter Höglinger, Planegg (DE); Matthias Höllerhage, Munich (DE); Thomas Werner Rösler, Munich (DE)

(73) Assignees: DEUTSCHES ZENTRUM FÜR NEURODEGENERATIVE ERKRANKUNGEN E. V. (DZNE), Bonn (DE); KLINIKUM RECHTS DER ISAR DER TECHNISCHEN UNIVERSITÄT MÜNCHEN, Munich (DE)

(*) Notice: Subject to any disclaimer, the term of this patent is extended or adjusted under 35 U.S.C. 154(b) by 0 days.

(21) Appl. No.: 16/340,929

(22) PCT Filed: Oct. 10, 2017

(86) PCT No.: PCT/EP2017/075800
§ 371 (c)(1),
(2) Date: Apr. 10, 2019

(87) PCT Pub. No.: WO2018/069312
PCT Pub. Date: Apr. 19, 2018

(65) Prior Publication Data
US 2019/0282552 A1  Sep. 19, 2019

(30) Foreign Application Priority Data
Oct. 11, 2016  (EP) .................................. 16193362

(51) Int. Cl.
*A61K 31/4375* (2006.01)
*A61P 25/28* (2006.01)
*A61K 31/519* (2006.01)
*C12N 15/113* (2010.01)
*A61K 31/713* (2006.01)

(52) U.S. Cl.
CPC ........ *A61K 31/4375* (2013.01); *A61K 31/519* (2013.01); *A61K 31/713* (2013.01); *A61P 25/28* (2018.01); *C12N 15/1137* (2013.01); *C12Y 301/04017* (2013.01); *C12N 2310/14* (2013.01)

(58) Field of Classification Search
CPC ............................ A61K 31/4353; A61P 25/28
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,474,960 A | 10/1984 | Szántay et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 7,354,918 B2 | 4/2008 | Ciapetti et al. | |
| 7,355,045 B2 | 4/2008 | Dey et al. | |
| 2007/0088046 A1 | 4/2007 | Ciapetti et al. | |
| 2009/0118171 A1* | 5/2009 | Zollo | A61K 31/475 514/1.1 |
| 2011/0190373 A1* | 8/2011 | Yan | A61K 31/4745 514/44 A |

FOREIGN PATENT DOCUMENTS

| | | |
|---|---|---|
| EP | 1 737 856 | 11/2010 |
| FR | 2 507 605 | 12/1982 |
| WO | WO 2006121985 | * 11/2006 |
| WO | 2009/003147 | 12/2008 |
| WO | 2009/137465 | 11/2009 |
| WO | 2013/076646 | 5/2013 |

OTHER PUBLICATIONS

Zawilska. Pharmacological Reports, 2013, 65, 1-14 (Year: 2013).*
Sanchesario. Neurochemistry International, 2014, 79, 44-56 (Year: 2014).*
Sharma. Neuroscience, 2015, 286, 393-403 (Year: 2015).*
Vasta. Biology of Reproduction, 2005, 73, 598-609 (Year: 2005).*
Siddiqui. Scientific Reports, 2016, 6:24475, 1-11 (Year: 2016).*
Berg et al., "*MDS Research Criteria for Prodromal Parkinson's Disease,*" Movement Disorders, vol. 30, No. 12, 2015, 1600-1609.
Bingham et al., "*Over one hundred solvates of sulfathiazole,*" Chem. Commun., 2001, 603-604 DOI: 10.1039/b009540k.
Hans Bundgaard, "(*C*) *Means to Enhance Penetration (1) Prodrugs as a means to improve the delivery of peptide drugs,*" Advanced Drug Delivery Reviews, 8 (1992) 1-38.
Caira et al., "*Preparation and Crystal Characterization of a Polymorph, a Monohydrate, and an Ethyl Acetate Solvate of the Antifungal Fluconazole,*" Journal of Pharmaceutical Sciences, vol. 93, No. 3, Mar. 2004, 601-611.

(Continued)

*Primary Examiner* — Noble E Jarrell
(74) *Attorney, Agent, or Firm* — Grüneberg and Myers PLLC

(57) ABSTRACT

A modulator of PDE1A and/or PDE1C can be used as a medicament, in particular in the prevention or treatment of synucleinopathies, such as multiple system atrophy, dementia with Lewy bodies, Parkinson's disease, pure autonomic failure, rapid eye movement sleep behavior disorder, inherited synucleinopathies caused by mutations or multiplications of the SNCA gene, or synucleinopathies caused by mutations in other genes including, but not limited to, GBA, LRRK2 and PARK2.

12 Claims, 5 Drawing Sheets

Figure 1:
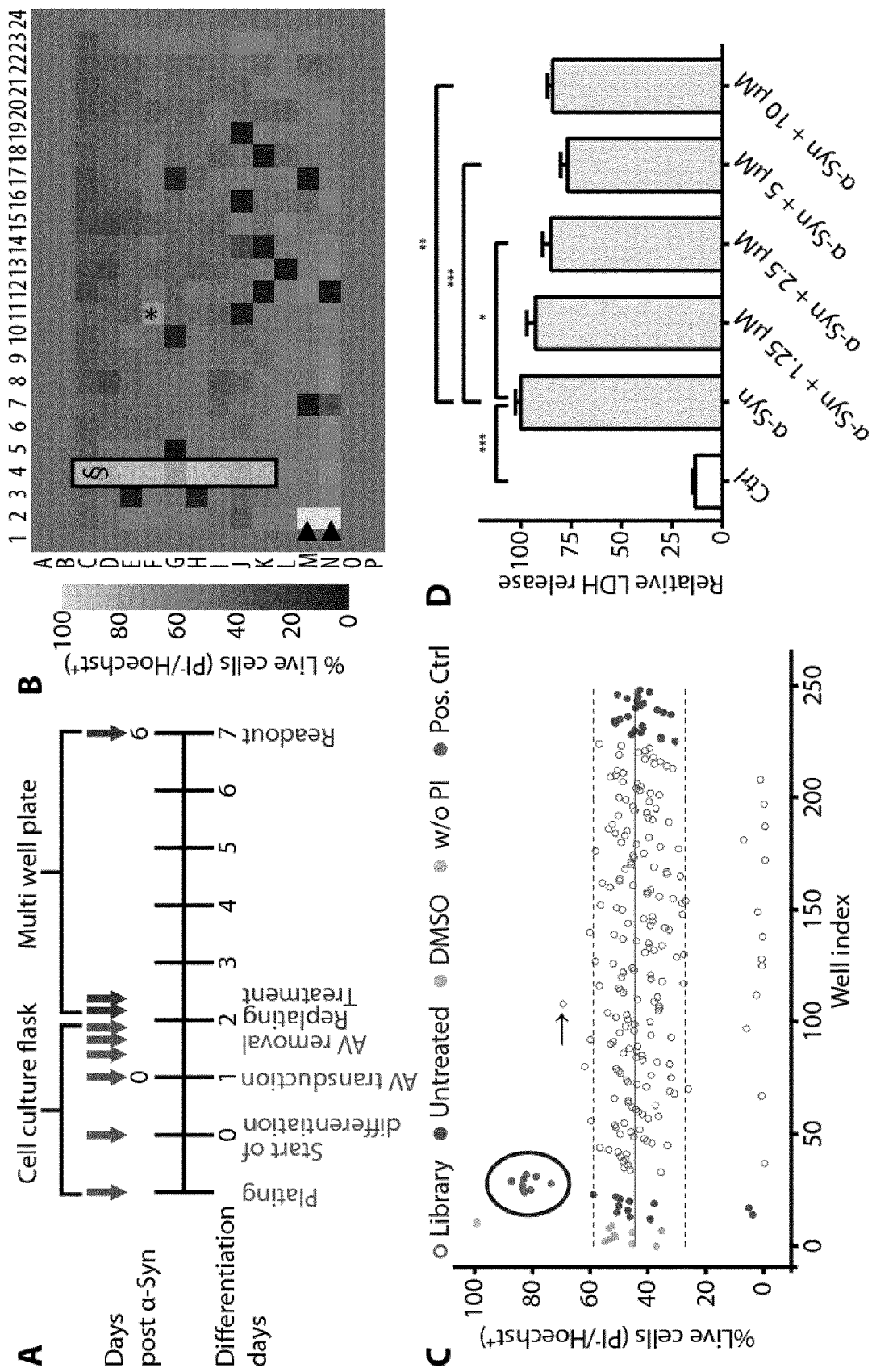

Specification includes a Sequence Listing.

(56) References Cited

OTHER PUBLICATIONS

De Souza et al., "Forskolin: A Labdane Diterpenoid with Antihypertensive, Positive Inotropic, Platelet Aggregation Inhibitory, and Adenylate Cyclase Activating Properties," Medicinal Research Reviews, vol. 3, No. 2, 201-219 (1983).
During et al., "Controlled Release of Dopamine from a Polymeric Brain Implant: In Vivo Characterization," Ann. Neurol., 1989; 25:351-356.
Gilman et al., "Second consensus statement on the diagnosis of multiple system atrophy," Neurology 2008; 71; 670-676 DOI 10.1212/01.wnl.0000324625.00404.15.
D. Giron, "Investigations of Polymorphism and Pseudo-Polymorphism in Pharmaceuticals by Combined Thermoanalytical Techniques," Journal of Thermal Analysis and Calorimetry, vol. 64 (2001) 37-60.
M. Goedert, "Alpha-Synuclein and Neurodegenerative Diseases," Nature Reviews, Neuroscience, vol. 2, Jul. 2001, 492-501.
J. Max Goodson, "Dental Applications," Medical Applications of Controlled Release, vol. 2, Applications and Evaluation, Chapter 6, pp. 115-138 (Langer and Wise, eds., CRC Press, 1984).
Halliday et al., "Neuropathology underlying clinical variability in patients with synucleinopathies," Acta Neuropathol (2011) 122:187-204 DOI 10.1007/s00401-011-0852-9.
Höllerhage et al., "Trifluoperazine rescues human dopaminergic cells from wild-type α-synuclein-induced toxicity," Neurobiology of Aging 35 (2014) 1700-1711.
Howard III et al., "Intracerebral drug delivery in rats with lesion-induced memory deficits," J. Neurosurg 71:105-112, 1989.
Iranzo et al., "Idiopathic rapid eye movement sleep behaviour disorder: diagnosis, management, and the need for neuroprotective interventions," Lancet Neurol 2016; 15: 405-19.
Kakeya et al., "Studies on Prodrugs of Cephalosporins. I. [1] Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid," Chem. Pharm. Bull. 32(2) 692-698 (1984).
Langer et al., "Chemical and Physical Structure of Polymers as Carriers for Controlled Release of Bioactive Agents: A Review," Journal of Macromolecular Science—Reviews in Macromolecular Chemistry and Physics, 23:1, 61-126, DOI: 10.1080/07366578308079439.
R. Langer, "New Methods of Drug Delivery," Science 249 (4976), 1527-1533, Sep. 28, 1990 DOI: 10.1126/science.2218494.
Levin et al., "The Differential Diagnosis and Treatment of Atypical Parkinsonism," Dtsch Arztebl Int 2016; 113: 61-9 DOI: 10.3238/arztebl.2016.0061.
Levy et al., "Inhibition of Calcification of Bioprosthetic Heart Valves by Local Controlled-Release Diphosphonate," Science 228 (4696), 190-192, Apr. 12, 1985 DOI: 10.1126/science.3919445.
Maurice et al., "Advances in targeting cyclic nucleotide phosphodiesterases," Nature Reviews. Drug Discovery. vol. 13, Apr. 2014, 290-314.
McKeith et al., "Diagnosis and management of dementia with Lewy bodies: Third report of the DLB consortium," Neurology 2005;65;1863-1872 DOI 10.1212/01.wnl.0000187889.17253.bl.
Neilsen et al., "Glycolamide Esters as Biolabile Prodrugs of Carboxylic Acid Agents: Synthesis, Stability, Bioconversion, and Physicochemical Properties," Journal of Pharmaceutical Sciences vol. 77, No. 4, Apr. 1988, 285-298.
Postuma et al., "Screening for prodromal Parkinson's disease in the general community: a sleep-based approach," Sleep Medicine 21 (2016) 101-105.
Radebaugh et al., "Preformulation," Remington: The Science and Practice of Pharmacy, Nineteenth Edition, vol. II, Chapter 83, pp. 1447-1462 (Mack Publishing, Easton, PA, 1995).
Saudek et al., "A Preliminary Trial of the Programmable Implantable Medication System for Insulin Delivery," The New England Journal of Medicine, Aug. 31, 1989, 574-579.
M. V. Sefton, "Implantable Pumps," CRC Critical Reviews in Biomedical Engineering, vol. 14, Issue 3, 201-240 (1987).
Sitges et al., "Effects of carbamazepine, phenytoin, valproic acid, oxcarbazepine, lamotrigine, topiramate and vinpocetine on the presynaptic $Ca^{2+}$ channel-mediated release of [$^3$H]glutamate: Comparison with the $Na^+$ channel-mediated release", Neuropharmacology 53 (2007) 854-862 doi:10.1016/j.neuropharm.2007.08.016.
Sitges et al., "Vinpocetine blockade of sodium channels inhibits the rise in sodium and calcium induced by 4-aminopyridine in synaptosomes," Neurochemistry International 46 (2005) 533-540 doi:10.1016/j.neuint.2005.02.001.
Smolen et al., "Drug Product Design and Performance," Controlled Drug Bioavailability vol. 1, 4 pages (John Wiley & Sons, New York, 1984).
Stasch et al., "NO-independent regulatory site on soluble guanylate cyclase," Nature vol. 410, Mar. 8, 2001, 212-215.
Tofaris et al., "Lysosome-Dependent Pathways as a Unifying Theme in Parkinson's Disease," Movement Disorders, vol. 27, No. 11, 2012, 1364-1369.
Treat et al., "Liposome Encapsulated Doxorubicin—Preliminary Results of Phase I and Phase II Trials" Liposomes in the Therapy of Infectious Disease and Cancer, pp. 353-365 (1989).
Wenning et al., "Development and Validation of the Unified Multiple System Atrophy Rating Scale (UMSARS)," Movement Disorders vol. 19, No. 12, 2004, pp. 1391-1402 DOI: 10.1002/mds.20255.
Van Tonder et al., "Preparation and Physicochemical Characterization of 5 Niclosamide Solvates and 1 Hemisolvate," AAPS PharmSciTech 2004; 5 (1) Article 12, 10 pages.
International Search Report dated Feb. 23, 2018 in PCT/EP2017/075800, 8 pp.
Written Opinion dated Feb. 23, 2018 in PCT/EP2017/075800, 13 pp.
Abusnina et al., "Anti-proliferative effect of curcumin on melanoma cells is mediated by PDE1A inhibition that regulates the epigenetic integrator UHRF1," Mol. Nutr. Food Res, 2011, 55, 1977-1689; XP55355748A; DOI 10.1002/mnfr.201100307.
Buchwald et al., "Long-term, continuous intravenous heparin administration by an implantable infusion pump in ambulatory patients with recurrent venous thrombosis," Surgery, vol. 88, Oct. 1980, pp. 507-516.
Hans Bundgaard, "Design and Application of Prodrugs," A Textbook of Drug Design and Development, (1991), Chapter 5, pp. 113-191.
Dunkern et al., "Characterization of inhibitors of phosphodiesterase 1C on a human cellular system," FEBS Journal 274 (2007) 4812-4824; XP55355618A; DOI: 10.1111/j.1742-4658.2007.06001.x.
Abdel-Hasseb A. Fayed, "Brain Trace Element Concentration of Rats Treated with the Plant Alkaloid, Vincamine," Biol Trace Elem Res (2010) 136:314-319; DOI: 10.1007/s12011-009-8550-3; XP55355224A.
C.N. Filer, "The Preparation and Characterization of Tritiated Neurochemicals,"Isotopes in the Physical and Biomedical Sciences, vol. 1, Labelled Compounds (Part A) (1987), Chapter 6, pp. 156-192.
Robert E. King, "Tablets, Capsules, and Pills," Chapter 89, Remington's Pharmaceutical Sciences, 16th Edition, Mack Publishing, Easton, PA, (1980) pp. 1553-1584.
Lopez-Berestein et al., "Treatment of Systemic Fungal Infections with Liposomal Amphotericin B," Arch Intern Med, vol. 149, Nov. 1989, pp. 2533-2536.
Alexandre E. Medina, "Therapeutic utility of phosphodiesterase type I inhibitors in neurological conditions," Frontiers in Neuroscience, Feb. 18, 2011, vol. 5, Article 21; DOI: 10.3389/fnins.2011.00021; XP55289492A.
Ono et al., "Anti-Fibrillogenic and Fibril-Destabilizing Activities of Anti-Parkinsonian Agents for α-Synuclein Fibrils in Vitro," Journal of Neuroscience Research 85:1547-4557 (2007); XP55355332A.
Sharma et al., "Vinpocetine Attenuates MPTP-Induced Motor Deficit and Biochemical Abnormalities in Wistar Rats," Neuroscience 286 (2015), 393-403; XP29188366A.

\* cited by examiner

SEQUENCE LISTING

```
<160> NUMBER OF SEQ ID NOS: 4

<210> SEQ ID NO 1
<211> LENGTH: 25
<212> TYPE: RNA
<213> ORGANISM: Artificial Sequence
<220> FEATURE:
<223> OTHER INFORMATION: siRNA Sequences against PDE1A sense

<400> SEQUENCE: 1
ccagcagcug ucaucguaac auuaa                                      25

<210> SEQ ID NO 2
<211> LENGTH: 25
<212> TYPE: RNA
<213> ORGANISM: Artificial Sequence
<220> FEATURE:
<223> OTHER INFORMATION: siRNA Sequences against PDE1A antisense

<400> SEQUENCE: 2
uuaauguuac gaugacagcu gcugg                                      25

<210> SEQ ID NO 3
<211> LENGTH: 25
<212> TYPE: RNA
<213> ORGANISM: Artificial Sequence
<220> FEATURE:
<223> OTHER INFORMATION: siRNA Sequences against PDE1C sense

<400> SEQUENCE: 3
caccagcugu uauugaggca uuaaa                                      25

<210> SEQ ID NO 4
<211> LENGTH: 25
<212> TYPE: RNA
<213> ORGANISM: Artificial Sequence
<220> FEATURE:
<223> OTHER INFORMATION: siRNA Sequences against PDE1C antisense

<400> SEQUENCE: 4
uuuaaugccu caauaacagc uggug                                      25
```

TREATMENT OF SYNUCLEINOPATHIES

This application is a National Stage entry under § 371 of International Application No. PCT/EP2017/075800, filed on Oct. 10, 2017, and which claims the benefit of European Application No. 16193362.7, filed on Oct. 11, 2016.

FIELD OF THE INVENTION

The present invention relates to a modulator of phosphodiesterase PDE1A and/or PDE1C for use as a medicament, in particular for use in the prevention or treatment of synucleinopathies, including, but not limited to multiple system atrophy, dementia with Lewy bodies, Parkinson's disease, pure autonomic failure, rapid eye movement sleep behavior disorder or inherited synucleinopathies caused by mutations or multiplications of the alpha-synuclein gene SNCA, or synucleinopathies caused by mutations in other genes including, but not limited to GBA, LRRK2 and PARK2. Modulators of PDE1A and/or PDE1C according to the invention include small molecules, such as compounds of formula (I), (II) or (III), as well as nucleic acids, such as siRNAs.

BACKGROUND OF THE INVENTION

Neurodegenerative diseases of the human brain are characterized by the degeneration of specific populations of nerve cells. The three main disease groups constituting the majority of neurodegenerative diseases are tauopathies, alpha-synucleinopathies (also referred to as synucleinopathies) and diseases due to repetitions of glutamine. It is believed that in synucleinopathies, α-synuclein (α-syn) confers toxicity via small oligomeric forms, which are intermediates between monomers and larger aggregates. α-syn is a 140 amino acids long presynaptic protein. Although its physiological function is not fully understood, it is clear that α-syn is an essential player in the pathophysiology of a group of neurodegenerative disorders termed synucleinopathies. Besides Parkinson's disease (PD), also other neurodegenerative disorders are characterized by the abnormal deposition of α-syn in neurons, namely multiple system atrophy (MSA), pure autonomic failure (PAF), rapid eye movement sleep behavior disorder (RBD) Parkinson's disease with dementia (PDD) and dementia with Lewy bodies (DLB). Histopathologically, α-syn is the main component of the intracellular inclusions called Lewy bodies or Lewy neurites, which characterize PD, PDD and DLB, and of glial cytoplasmic inclusions, which characterize MSA.

Up to today, there is no therapy available to slow or halt the progression of synucleinopathies. Therefore, there is the need of novel therapeutic approaches against α-syn-mediated neurodegeneration.

OBJECTIVES AND SUMMARY OF THE INVENTION

The present invention provides compounds for the treatment or prevention of synucleinopathies. The invention is based on the inventor's finding that inhibition of PDE1A and/or PDE1C activity or reduced expression of PDE1A and/PDE1C counteracts the abnormal deposition of α-syn. Accordingly, by reducing the activity or expression of PDE1A and/or PDE1C abnormal deposition of α-syn can be reduced or avoided. Hence, the compounds of the invention i.e. modulators of PDE1A and/or PDE1C, in particular by inhibitors of PDE1A and/or PDE1C can be used for the prevention or treatment of medical conditions involving the abnormal deposition of α-syn. Thus, according to the invention modulators of PDE1A and/or PDE1C, in particular inhibitors of PDE1A and PDE1C can be used for the prevention or treatment of synucleinopathies, such as MSA, DLB, PD, PAF, RBD or inherited synucleinopathies caused by mutations or multiplications of the α-syn gene SNCA, or synucleinopathies caused by mutations in other genes including, but not limited to GBA, LRRK2 and PARK2. Modulators of PDE1A and/or PDE1C are advantageous, since due to their specificity for the PDE1A and/or PDE1C isoform, they may cause less side effects and therefore are preferred for the treatment of synucleinopathies.

Further, the results of the present invention show that vinpocetine can reduce abnormal deposition of α-syn and therefore protects dopaminergic neurons from α-syn induced toxicity. Therefore, vinpocetine is useful in the prevention or treatment of MSA, DLB, PD, PAF, RBD, or inherited synucleinopathies caused by mutations or multiplications of the α-syn gene SNCA, or synucleinopathies caused by mutations in other genes including, but not limited to GBA, LRRK2 and PARK2.

Hence a first aspect of the invention refers to a compound for use as a medicament, wherein the compound is a PDE1A modulator and/or a PDE1C modulator.

In particular, the invention refers to a PDE1A modulator for use in the prevention or the treatment of a medical condition. In some embodiments the PDE1A is a human PDE1A. In the specific embodiment the compound is a selective PDE1A modulator, preferably a PDE1A inhibitor.

The invention also refers to a PDE1C modulator for use in the prevention or the treatment of a medical condition. In some embodiments the PDE1C is a human PDE1C. In the specific embodiment the compound is a selective PDE1C modulator, preferably a PDE1C inhibitor.

Some embodiments refer to a compound for use according to the invention, wherein the compound is represented by the following formula (I)

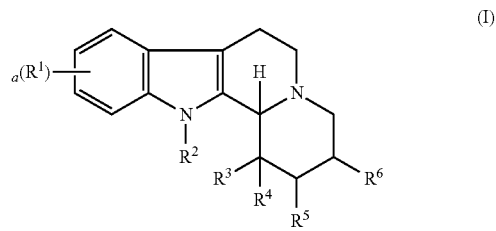

wherein
R$^1$ is selected from the group consisting of —H and halo, a is 0, 1, 2, or 3, and preferably 0 or 1
R$^2$ is selected from the group consisting of —H and —(C$_1$-C$_6$)alkyl,
R$^3$ and R$^4$ are independently selected from the group consisting of —H, —OH, —(C$_1$-C$_6$)alkyl, and —(C$_1$-C$_6$)-hydroxyalkyl, or
R$^3$ and R$^4$ taken together are =O, or
R$^2$ and R$^3$ together with the nitrogen atom and carbon atom they are attached to form a 6-membered heterocyclic ring which is optionally substituted,
R$^5$ and R$^6$ are independently selected from the group consisting of —H and —(C$_1$-C$_6$)alkyl, or
R$^5$ and R$^6$ taken together form a carbon-carbon bond, or a pharmaceutically acceptable derivative thereof, wherein the alkyl and hydroxyalkyl groups are optionally substituted and wherein the compound is not vinpocetine.

In specific embodiments, the 6-membered heterocyclic ring is optionally substituted with 1, 2, or 3 substituents selected from the group consisting of —COOR$^7$, —OH and —(C$_1$-C$_6$)alkyl, wherein R$^7$ is selected from the group consisting of —H, —(C$_1$-C$_{12}$)alkyl, —(C$_2$-C$_{12}$)alkenyl, —(C$_2$-C$_{12}$)alkynyl, —(C$_1$-C$_{12}$)alkyl-ONO$_2$, —(C$_2$-C$_{12}$)alkenyl-ONO$_2$, —(C$_2$-C$_{12}$)alkynyl-ONO$_2$, (6 to 14 membered)aryl, (5 to 10 membered)heteroaryl, trimethoxyphenyl, —(C$_1$-C$_6$)alkyl-(6 to 14 membered)aryl and —(C$_1$-C$_6$)alkyl-(5-10 membered)heteroaryl, wherein the alkyl, alkenyl, alkynyl, aryl and heteroaryl groups are optionally substituted.

In particular, the invention refers to a compound for use according to the invention, wherein the compound is represented by the following formula (II)

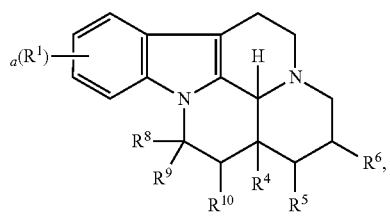

(II)

wherein

R$^1$ is selected from the group consisting of —H and halo, a is 0, 1, 2, or 3, and preferably 0 or 1

R$^8$ is COOR$^7$,

R$^9$ and R$^{10}$ are independently selected from the group consisting of —H, —OH and —(C$_1$-C$_6$)alkyl, or R$^9$ and R$^{10}$ taken together form a carbon-carbon bond, R$^4$ is selected from the group consisting of —H, —OH, —(C$_1$-C$_6$)alkyl, and (C$_1$-C$_6$)-hydroxyalkyl, R$^5$ and R$^6$ are independently selected from the group consisting of —H and —(C$_1$-C$_6$)alkyl, or R$^5$ and R$^6$ taken together form a carbon-carbon bond, R$^7$ is selected from the group consisting of —H, —(C$_1$-C$_{12}$)alkyl, —(C$_2$-C$_{12}$)alkenyl, —(C$_2$-C$_{12}$)alkynyl, —(C$_1$-C$_{12}$)alkyl-ONO$_2$, —(C$_2$-C$_{12}$)alkenyl-ONO$_2$, —(C$_2$-C$_{12}$)alkynyl-ONO$_2$, (6 to 14 membered)aryl, (6 to 14 membered)heteroaryl, trimethoxyphenyl, —(C$_1$-C$_6$)alkyl-(6 to 14 membered)aryl and —(C$_1$-C$_6$)alkyl-(6 to 14 membered)heteroaryl or a pharmaceutically acceptable derivative thereof, wherein the alkyl, alkenyl, alkynyl, aryl and heteroaryl groups are optionally substituted.

Another embodiment refers to a compound for use according to the invention wherein the compound is represented by the following formula (III)

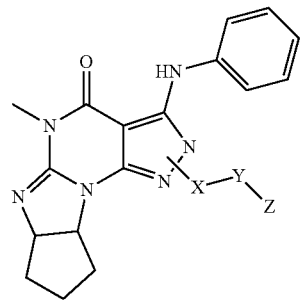

(III)

wherein

X is —(C$_1$-C$_6$)alkylene;

Y is a single bond, —(C$_2$-C$_{12}$)alkenylene, —(C$_2$-C$_{12}$)alkynylene, —(C$_6$-C$_{14}$)arylene or -(5- to 10 membered) heteroarylene;

Z is H, -(6 to 14 membered)aryl, -(5 to 10 membered) heteroaryl, halo, halo(C$_1$-C$_6$)alkyl, —C(O)—R$^1$, —N(R$^2$)(R$^3$), or —(C$_3$-C$_7$)cycloalkyl, wherein the —(C$_3$-C$_7$)cycloalkyl optionally comprises at least one heteroatom selected from a group consisting of N or O;

R$^1$ is —(C$_1$-C$_6$)alkyl, halo(C$_1$-C$_6$)alkyl;

R$^2$ and R$^3$ are independently selected from H or —(C$_1$-C$_6$)alkyl, wherein X, Y and Z are independently and optionally substituted with halo, or a pharmaceutically acceptable derivative thereof.

A specific embodiment refers to a compound for use according to the invention, wherein the compound is

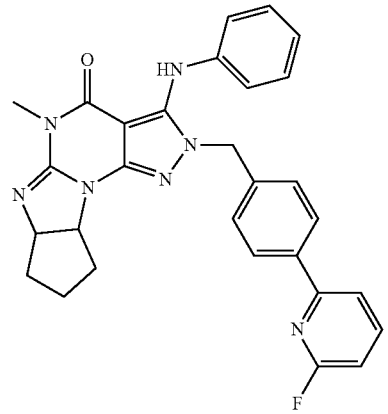 [SMILES: CN1C(=O)c2c(nn(Cc3ccc(-c4cccc(F)n4)cc3)c2Nc2ccccc2)N2C1=NC1CCCC12]

or a pharmaceutically acceptable derivative thereof.

Another embodiment of the invention refers to a nucleic acid for use according to the invention. In one embodiment the compound is RNA. In a specific embodiment the RNA is single-stranded or double-stranded RNA. The RNA may be selected from the group consisting of viral RNA, retroviral RNA, small interfering RNA (siRNA), antisense RNA, aptamers, microRNA (miRNA), double-stranded RNA (dsRNA), small hairpin RNA (shRNA), and Piwi-interacting RNA (piRNA). Preferably, the RNA is selected from the group consisting of siRNA, antisense RNA, dsRNA, and shRNA, more preferably siRNA.

In a specific embodiment of the invention the RNA comprises or consists of a nucleotide sequence which exhibits at least 50%, at least 60%, at least 70%, at least 80%, at least 85%, at least 90%, at least 95%, at least 96%, at least 97%, at least 98%, or at least 99% identity to the sequence according to SEQ ID NO: 1 and/or SEQ ID NO: 3. In a more specific embodiment of the invention, the RNA comprises or consists of a nucleotide sequence of SEQ ID NO: 1 and/or SEQ ID NO: 3. Typically, the nucleic acid is a synthetic nucleic acid. The nucleic acid may be an isolated nucleic acid.

In one embodiment of the invention the medical condition is a synucleinopathy. Preferably, the synucleinopathy is selected from Parkinson's disease (PD), Parkinson's disease with dementia (PDD), multiple system atrophy (MSA), dementia with Lewy bodies (DLB), pure autonomic failure (PAF), rapid eye movement sleep behavior disorder (RBD), or inherited synucleinopathies caused by mutations or multiplications of the α-syn gene SNCA, or synucleinopathies caused by mutations in other genes including, but not limited to GBA, LRRK2 and PARK2.

More preferably the synucleinopathy is MSA or rapid eye movement sleep behavior disorder (RBD). In one embodiment the synucleinopathy is MSA. The multiple system atrophy (MSA) is selected from MSA with predominantly cerebellar symptoms (MSA-C), MSA with predominantly parkinsonian symptoms (MSA-P).

In one embodiment, the synucleinopathy is rapid eye movement sleep behavior disorder (RBD).

In one embodiment, the synucleinopathy is RBD, without tremor. In one embodiment, the synucleinopathy is RBD without bradykinesia, rigidity, tremor and postural instability. In one embodiment, the synucleinopathy is RBD wherein no symptoms of Parkinson's disease are present.

Another embodiment refers to an isolated vector encoding the RNA for use according to the invention.

Another aspect refers to a compound of Formula (I)

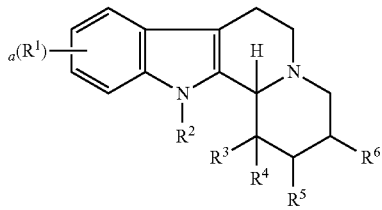

(I)

wherein
$R^1$ is selected from the group consisting of —H and halo, a is 0, 1, 2, or 3, and preferably 0 or 1
$R^2$ is selected from the group consisting of —H and —($C_1$-$C_6$)alkyl,
$R^3$ and $R^4$ are independently selected from the group consisting of —H, —OH, —($C_1$-$C_6$)alkyl, and —($C_1$-$C_6$)-hydroxyalkyl, or
$R^3$ and $R^4$ taken together are =O, or
$R^2$ and $R^3$ together with the nitrogen atom and carbon atom they are attached to form a 6-membered heterocyclic ring which is optionally substituted,
$R^5$ and $R^6$ are independently selected from the group consisting of —H and —($C_1$-$C_6$)alkyl, or
$R^5$ and $R^6$ taken together form a carbon-carbon bond,
or a pharmaceutically acceptable derivative thereof, wherein the alkyl and hydroxyalkyl groups are optionally substituted
and wherein the compound is not vinpocetine.

In one embodiment, $R^2$ and $R^3$ together with the nitrogen atom and the carbon atom they are attached to for a 6-membered heterocyclic ring, the 6-membered heterocyclic ring may be substituted with 1, 2, or 3 substituents independently selected from the group consisting of —COOR$^7$, —OH and —($C_1$-$C_6$)alkyl;
wherein $R^7$ is selected from the group consisting of. —H, —($C_1$-$C_{12}$)alkyl, —($C_2$-$C_{12}$)alkenyl, —($C_2$-$C_{12}$)alkynyl, —($C_1$-$C_{12}$)alkyl-ONO$_2$, —($C_2$-$C_{12}$)alkenyl-ONO$_2$, —($C_2$-$C_{12}$)alkynyl-ONO$_2$, (6 to 14 membered)aryl, (5 to 10 membered)heteroaryl, trimethoxyphenyl, —($C_1$-$C_6$)alkyl-(6 to 14 membered)aryl and —($C_1$-$C_6$)alkyl-(5-10 membered) heteroaryl,
wherein the alkyl, alkenyl, alkynyl, aryl and heteroaryl groups are optionally substituted.

In one embodiment, the compound is represented by the following formula (II)

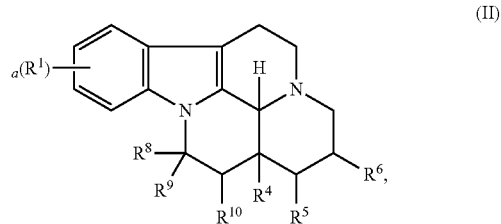

(II)

wherein
$R^1$ is selected from the group consisting of —H and halo, a is 0, 1, 2, or 3, and preferably 0 or 1
$R^8$ is COOR$^7$,
$R^9$ and $R^{10}$ are independently selected from the group consisting of —H, —OH and —($C_1$-$C_6$)alkyl, or
$R^9$ and $R^{10}$ taken together form a carbon-carbon bond,
$R^4$ is selected from the group consisting of —H, —OH, —($C_1$-$C_6$)alkyl, and ($C_1$-$C_6$)-hydroxyalkyl,
$R^5$ and $R^6$ are independently selected from the group consisting of —H and —($C_1$-$C_6$)alkyl, or
$R^5$ and $R^6$ taken together form a carbon-carbon bond,
$R^7$ is selected from the group consisting of —H, —($C_1$-$C_{12}$)alkyl, —($C_2$-$C_{12}$)alkenyl, —($C_2$-$C_{12}$)alkynyl, —($C_1$-$C_{12}$)alkyl-ONO$_2$, —($C_2$-$C_{12}$)alkenyl-ONO$_2$, —($C_2$-$C_{12}$) alkynyl-ONO$_2$, (6 to 14 membered)aryl, (6 to 14 membered) heteroaryl, trimethoxyphenyl, —($C_1$-$C_6$)alkyl-(6 to 14 membered)aryl and —($C_1$-$C_6$)alkyl-(6 to 14 membered) heteroaryl
or a pharmaceutically acceptable derivative thereof,
wherein the alkyl, alkenyl, alkynyl, aryl and heteroaryl groups are optionally substituted.

In one embodiment, the compound is represented by the following formula (III)

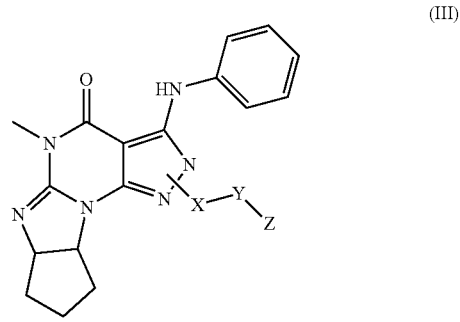

(III)

wherein

X is —($C_1$-$C_6$)alkylene;

Y is a single bond, —($C_2$-$C_{12}$)alkenylene, —($C_2$-$C_{12}$) alkynylene, —($C_6$-$C_{14}$)arylene or -(5- to 10 membered) heteroarylene;

Z is H, -(6 to 14 membered)aryl, -(5 to 10 membered) heteroaryl, halo, halo($C_1$-$C_6$)alkyl, —C(O)—$R^1$, —N($R^2$)($R^3$), or —($C_3$-$C_7$)cycloalkyl, wherein the —($C_3$-$C_7$)cycloalkyl optionally comprises at least one heteroatom selected from a group consisting of N or O;

$R^1$ is —($C_1$-$C_6$)alkyl, halo($C_1$-$C_6$)alkyl;

$R^2$ and $R^3$ are independently selected from H or —($C_1$-$C_6$)alkyl, wherein X, Y and Z are independently and optionally substituted with halo, or a pharmaceutically acceptable derivative thereof.

Another aspect of the invention refers to a composition comprising one or more compounds as described herein and a pharmaceutically acceptable carrier.

Another aspect of the invention refers to vinpocetine or a pharmaceutically acceptable derivative thereof for use in the treatment of a synucleinopathy selected from the group including but not limited to MSA, DLB, PD, PAF, RBD, and inherited synucleinopathies caused by mutations or multiplications of the α-syn gene SNCA, or synucleinopathies caused by mutations in other genes including, but not limited to GBA, LRRK2 and PARK2. Another aspect of the invention refers to vinpocetine or a pharmaceutically acceptable derivative thereof for use in the treatment of a synucleinopathy selected from the group consisting of MSA, DLB, PD, PAF, RBD, and inherited synucleinopathies caused by mutations or multiplications of the α-syn gene SNCA, or synucleinopathies caused by mutations in other genes including, but not limited to GBA, LRRK2 and PARK2. One embodiment refers to vinpocetine or a pharmaceutically acceptable derivative thereof for use in the treatment of a synucleinopathy selected from the group consisting of MSA, DLB, PAF and RBD. One embodiment refers to vinpocetine or a pharmaceutically acceptable derivative thereof for use in the treatment of a synucleinopathy selected from the group consisting of MSA and RBD. One embodiment refers to vinpocetine or a pharmaceutically acceptable derivative thereof for use in the treatment of MSA. The specific embodiment MSA is selected from MSA with predominantly cerebellar symptoms (MSA-C) and MSA with predominantly parkinsonian symptoms (MSA-P), preferably MSA-C.

In one embodiment, the present invention refers to vinpocetine or a pharmaceutically acceptable derivative thereof for use in the treatment of RBD.

In one embodiment, the present invention refers to vinpocetine or a pharmaceutically acceptable derivative thereof for use in the treatment of RBD, without tremor. In one embodiment the present invention refers to vinpocetine or a pharmaceutically acceptable derivative thereof for use in the treatment of RBD without bradykinesia, rigidity, tremor and postural instability. In one embodiment the present invention refers to vinpocetine or a pharmaceutically acceptable derivative thereof for use in the treatment of RBD wherein no symptoms of Parkinson's disease are present.

Another aspect of the invention refers to a composition comprising vinpocetine or a pharmaceutically acceptable derivative thereof and a pharmaceutically acceptable carrier for use according to the invention.

FIGURE LEGENDS

FIG. 1 High-throughput screening of N=1.600 FDA-approved drugs for modulators of α-syn toxicity in postmitotic human dopaminergic neurons. (A) Experimental design. Grey arrows indicate pipetting steps conducted in cell culture flasks or in multi-well plates, respectively. (B) Representative heat map showing cell survival in shades from bright (100% survival) to dark (0% survival) in wells containing α-syn transduced LUHMES neurons. Grey wells contained no cells. Hoechst 33342 was used to label all cells. Propidium iodide (PI) was used to label dead cells. In the two wells marked with arrow heads (▶) PI was omitted (100% survival controls). Survival rate was quantified as percentage of PP cells of all Hoechst$^+$ cells. The black frame and § denotes wells treated with a previously identified protective positive control compound (positive control). Asterix (*) denotes a hit compound providing neuroprotection. (C) Representative scatterplot showing cell survival quantitatively. Continuous line: mean survival of α-syn transduced neurons. Upper dashed line: Z-score of +2.5 (threshold for positive hit). Lower dashed line: Z-score of −3 (threshold for negative hit). Bright grey dots: wells treated with solvent (DMSO) only. Grey dots in the upper left corner: wells without PI. Dark grey dots outside the encircled area: wells without treatment. Dark grey dots in the encircled area: wells treated with a protective positive control compound. Blank dots: wells treated with compounds from the library. Arrow (→): hit compound (* in B). (D) Verification of the protective efficacy of the top hit dipyridamole in a dose range of 1.25 μM to 10 μM against α-syn-induced toxicity by quantification of LDH release into the medium. First column: LDH release of untransduced cells (Ctrl). *P<0.05, P<0.01, *P<0.001, one-way ANOVA with Tukey's HSD post-hoc test. Data are mean±s.e.m.

Figure 2:
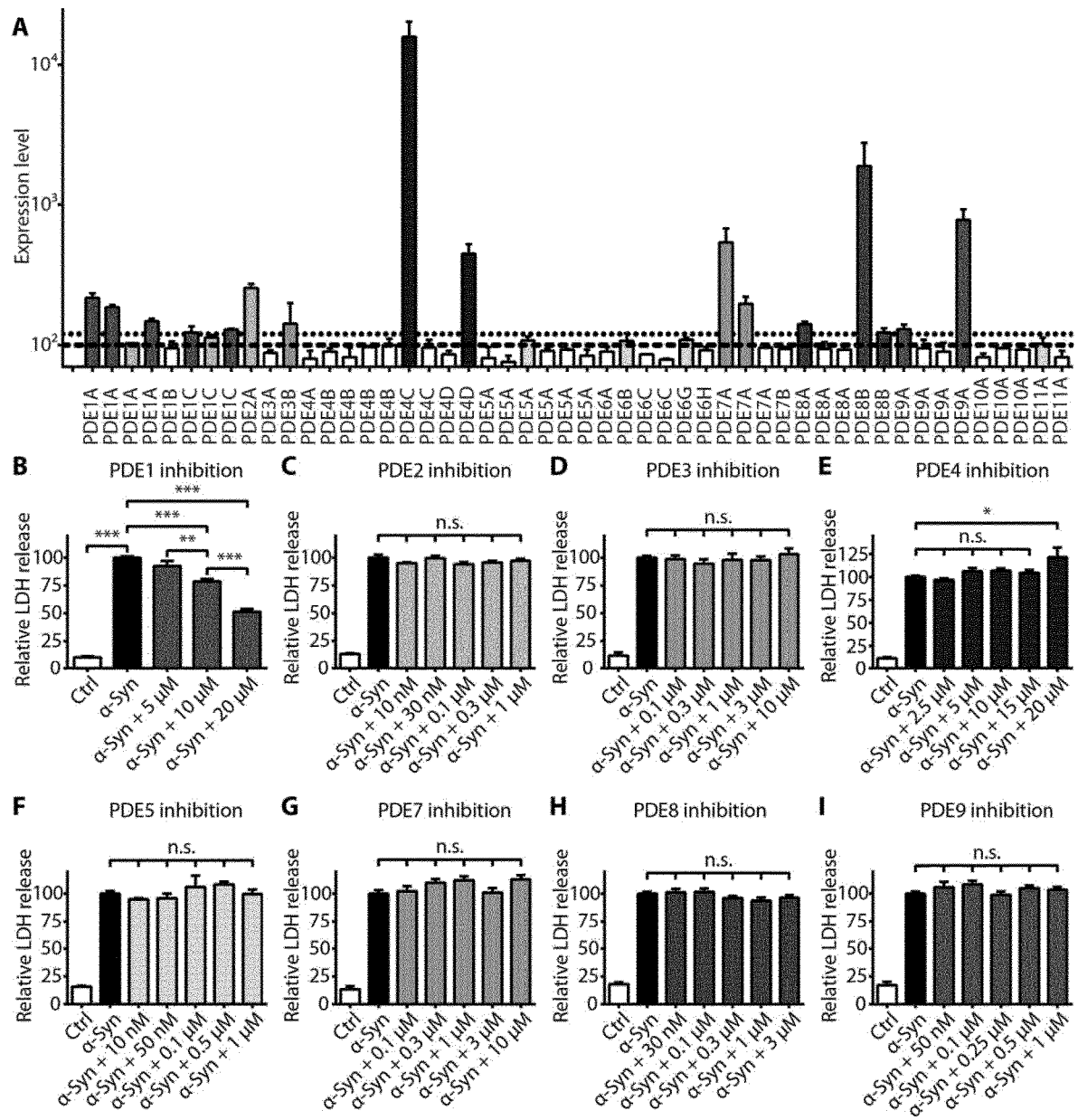

FIG. 2 Phosphodiesterase (PDE) 1 inhibition protects against α-syn toxicity. (A) Expression of the known PDE isoforms in LUHMES cells four days after transduction with α-syn. Bars in grey indicate PDEs with solid expression levels above the threshold of 120 arbitrary units (dotted line). The dashed line (100 units) indicates the threshold for background levels; blank bars indicate PDEs below this detection threshold. The area between the dashed and dotted lines indicate very low expression levels (bright grey bars). (B-I) LDH release as measure of α-syn-induced cell death, without or with treatment with different PDE inhibitors. Bars indicate untransduced control neurons (Ctrl, white bars), neurons overexpressing α-syn treated with solvent only (black bars), or with different PDE inhibitors (grey bars): PDE1: vinpocetine, PDE2: Bay60-7550, PDE3: milrinon, PDE4: rolipram, PDE5: sildenafil, PDE7: BRL50481, PDE8: PF-4957325-00, PDE9: Bay73-6691. Only vinpocetine protected from α-syn-induced toxicity. Data are normalized to LDH release in α-syn transduced cells with solvent treatment. *P<0.05, P<0.01, *P<0.001, n.s. not significant, one-way ANOVA with Tukey's HSD post-hoc test. Data are mean±s.e.m.

Figure 3:
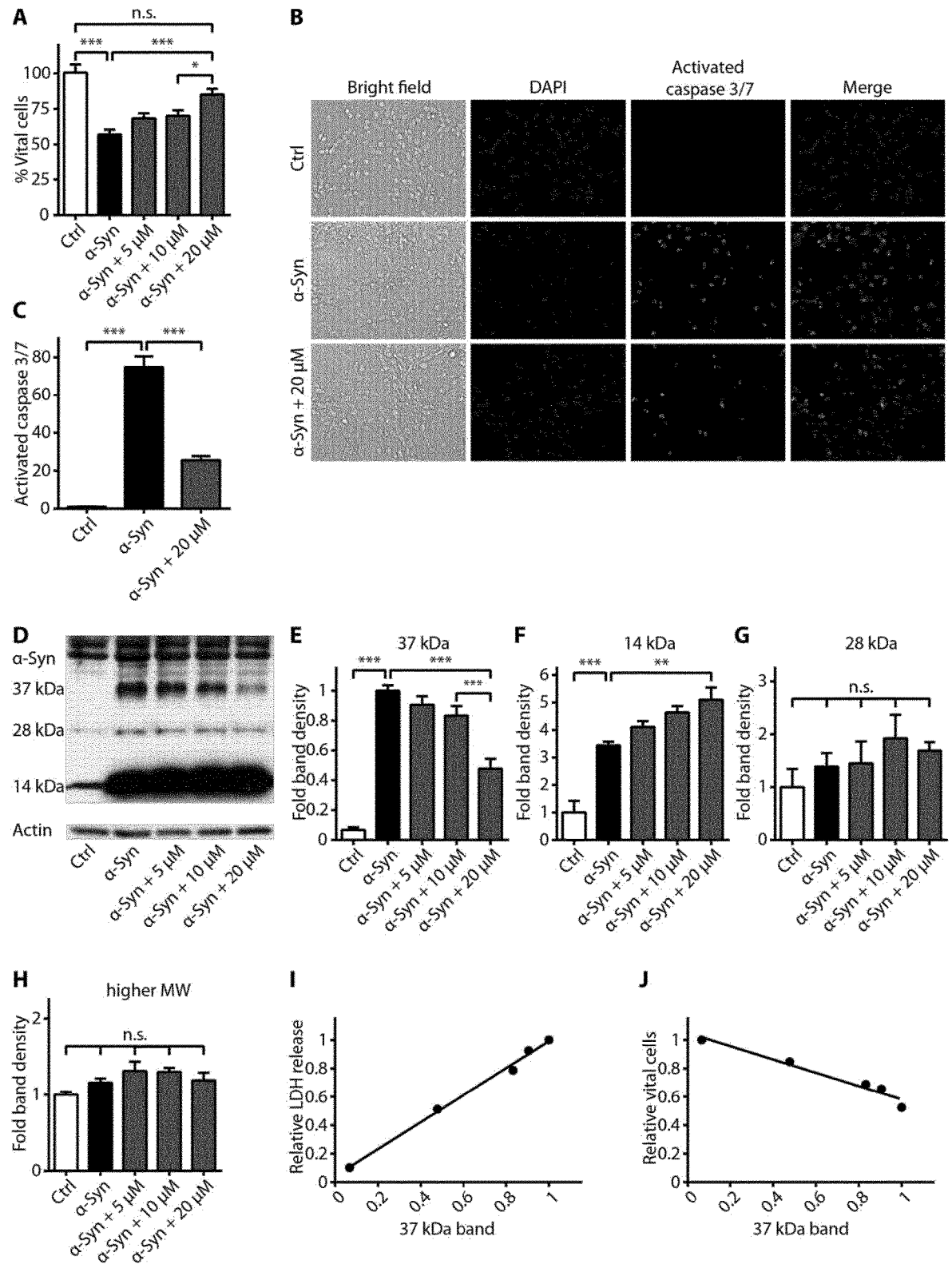

FIG. 3 The PDE1 inhibitor vinpocetine reduces cell death and 37 kDa α-syn specimen. (A) Cell counts of untransduced control cells (Ctrl, white bar), solvent treated α-syn transduced cells (black bar) and α-syn transduced cells with treated with different concentrations of vinpocetine (dark grey bars) confirmed the protective effect of vinpocetine. (B) Staining with CellEvent™ showed activation of caspases 3 and 7 in α-syn overexpressing cells, and a reduction of their activation by co-treatment with 20 μM vinpocetine. (C) Quantification of the CellEvent™ signal in untransduced control cells (Ctrl, left bar), α-syn transduced cells treated with solvent (black bar) and vinpocetine treated α-syn transduced cells (dark grey bar). (D) Representative Western blot of control cells (Ctrl), α-syn transduced cells without or with treatment vinpocetine in different concentrations. (E-H) Quantification of specific α-syn positive Western blot bands. Note that vinpocetine treatment reduced a 37 kDa α-syn band (E), increased the monomer α-syn band (F), and did not change other α-syn bands (G,H). The density of the 37 kDa band positively correlated with the LDH release ($r^2$=0.99, P<0.001, I) and negatively correlated with the number of vital cells ($r^2$=0.96, P<0.01, J). *P<0.05, P<0.01, *<0.001, n.s. not significant, one-way ANOVA with Tukey's HSD post-hoc test. Data are mean±s.e.m.

Figure 4:
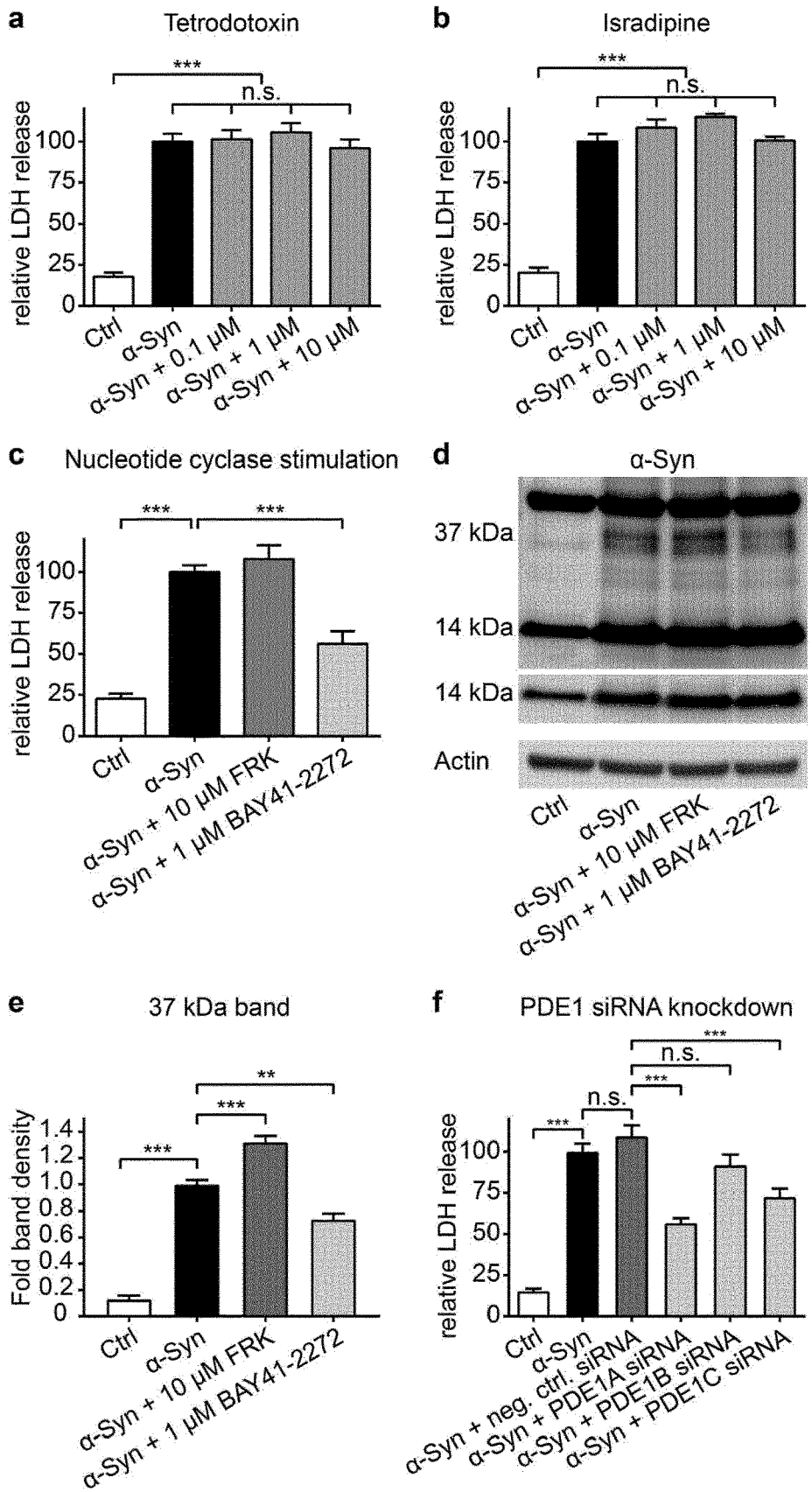

FIG. 4 Relevance of known mechanisms of action of vinpocetine for its protective efficacy. The figures (a-f) show the LDH release from LUHMES neurons into the medium as measure for toxicity. Untransduced control cells (Ctrl) are shown as white bars, solvent treated α-syn transduced cells with black bars, and α-syn transduced cells with different interventions in grey bars. Treatment with the sodium channel blocker tetrodotoxin (a, TTX, grey bars) and the calcium channel blocker isradipine (b, grey bars) in different concentrations did not protect against α-syn-induced toxicity. Treatment with 10 µM of the adenylate cyclase stimulator forskolin (c, FRK, third bar) did also not protect, while 1 µM of the guanylate cyclase stimulator BAY41-2272 (c, fourth bar) significantly reduced α-syn-induced toxicity. (d) Western blot with an α-Syn antibody (C20, Santa Cruz) of untransduced control neurons (Ctrl), α-Syn-transduced neurons treated with solvent (second lane), and α-Syn-transduced neurons with forskolin (FRK) or BAY41-2272 showed that BAY41-2272 treatment also led to a reduction of a 37 kDa α-Syn band, while forskolin led to an increase of this band. (e) Quantification of the 37 kDa band. (f) A negative control siRNA and siRNA against PDE1B did not protect against α-syn-induced toxicity, but siRNA against PDE1A was strongly protective, and siRNA against PDE1C was moderately protective against α-syn-induced toxicity. ***P<0.001, n.s. not significant, one-way ANOVA with Tukey's HSD post-hoc test. N-values, F-values and degrees of freedom (DF): (a) N=7, F=116.1, DF=30, (b) N=6, F=56.97, DF=25, (c) N=9, F=40.5, DF=32, (d), N=4, F=168.4, DF=12, (f) N≥9, F=69.79, DF=92. Data are mean±s.e.m.

Figure 5:
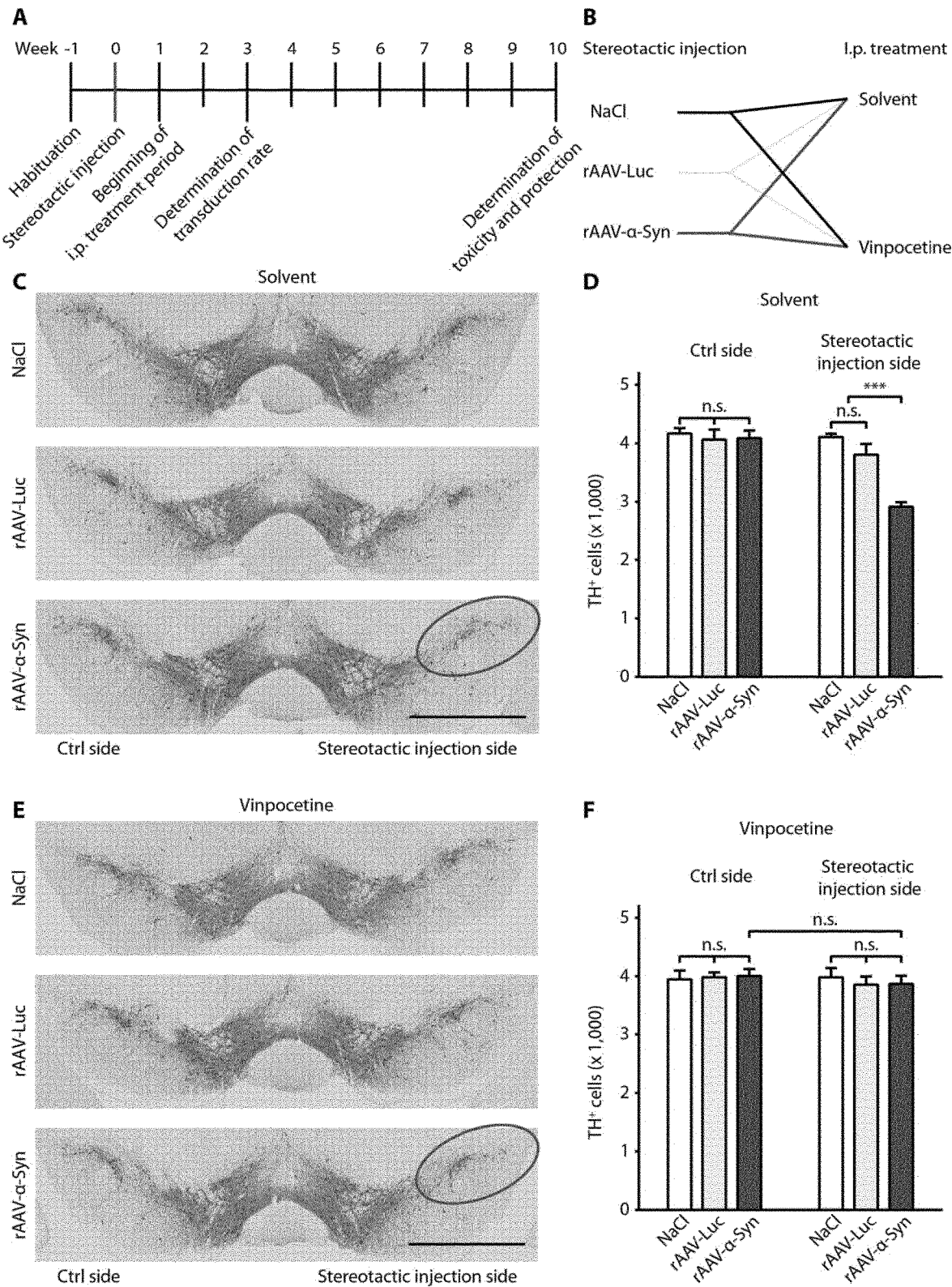

FIG. 5 Vinpocetine protects against α-syn-induced toxicity in vivo. (A) Experimental time flow. Grey bar: time point of stereotactical injection. (B) Experimental groups. Mice were injected stereotactically with either NaCl (control injection) or rAAV to overexpress luciferase (rAAV-Luc, control protein), or alpha-synuclein (rAAV-α-syn). Animals of each injection group were then randomized with a 1:1 allocation to be treated with once daily intraperitoneal injections of either solvent or vinpocetine for a 9-week period. (C) Representative images of the substantia nigra, immunostained for tyrosine hydroxylase (TH, grey) to identify dopaminergic neurons in solvent treated mice. Circle: area of cell loss upon α-syn overexpression. (D) Quantification of TH⁺ cells on the control (Ctrl) side and the stereotactic injection side of solvent treated mice. On the injection side there was a significant loss of TH⁺ cells (dark grey bar, right panel) after α-syn overexpression. (E) Images of the TH-immunostained substantia nigra of vinpocetine treated mice of the three injection groups. Circle: in contrast to solvent treated mice, vinpocetine treated mice showed no decline of TH⁺ neurons upon α-syn overexpression. (F) Quantification of the number of TH⁺ cells on the control (Ctrl) side and the stereotactic injection side of vinpocetine treated mice. Vinpocetine completely prevented α-syn-induced cell death. *P<0.05, ***P<0.001, n.s. not significant, two-way ANOVA with Tukey's HSD post-hoc test. Data are mean±s.e.m. Scale bars: 1 mm.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term "typically" indicates deviation from the indicated numerical value of ±10%, and preferably of ±5%.

Technical terms are used by their common sense. If a specific meaning is conveyed to certain terms, definitions of terms will be given in the following in the context of which the terms are used.

A first aspect of the invention refers to a modulator of PDE1A and/or PDE1C for use as a medicament.

The term "PDE1A" refers to the A isoform of phosphodiesterase 1 (PDE1). The sequence of PDE1A is set forth in NCBI Reference sequence: NC_000002.12, NC_018913.2.

The term "PDE1C" refers to C isoform of PDE1. The sequence of PDE1C is set forth in RefSeqGene: NG_051183.1.

The term "compound of the invention" refers to a modulator of PDE1A and/or PDE1C.

In some embodiments the modulator may be a small molecule, a binding protein, an antibody, or a nucleic acid. In some embodiments, the term encompasses compound of the group of vincamines, the compounds of formula (I), formula (II) and formula (III). In one embodiment the term means vinpocetine.

The term "modulator" refers to an inhibitor or activator of PDE1A and/or PDE1C.

The terms "modulate", "modulating", and the like as used herein with respect to the PDE1A and/or PDE1C phosphodiesterase mean the mediation of a pharmacodynamic response in an animal from (i) inhibiting or activating the phosphodiesterase, or (ii) directly or indirectly affecting the normal regulation of the phosphodiesterase activity (iii) directly or indirectly affecting the expression of PDE1A and/or PDE1C.

The term modulator of PDE1A and/or PDE1C, in particular the term selective modulator of PDE1A and/or PDE1C, refers to a compound that is specifically modulating the activity and/or expression of the PDE1A and/or PDE1C isoforms of PDE1. Therefore, the modulator of PDE1A and/or PDE1C may not modulate other PDE1 isoforms or other PDE types at all, and/or the modulator modulates PDE1A and/or PDE1C to a significantly higher extent than it modulates other PDE1 isoforms or other PDE types. For example, the modulation of PDE1A and/or PDE1C may be 30%, 40%, 50%, 60%, 70%, 80%, 90%, 100%, 150%, 200%, 300%, 400%, 500% or more, higher than the modulation of a different PDE1 isoform, such as PDE1B, or other PDE types.

The term "inhibitor" refers to a compound that reduces expression or activity of the PDE1A and/or PDE1C. The term thus may include small molecule inhibitors, antibodies or nucleotides, such as siRNAs. In particular, the term may include small molecules and siRNAs. Antibodies may include monoclonal antibodies, humanized antibodies, and Ig fusion proteins.

By "reduce the expression or activity of PDE1A and/or PDE1C" is meant to reduce the level or biological activity of PDE1A and/or PDE1C relative to the level or biological activity of PDE1A and/or PDE1C in an untreated control. According to this invention, such level or activity is reduced by at least 10%, 20%, 30%, 40%, 50%, 60%, 70%, 80%, 90%, 100%, or even greater than 100%, relative to an untreated control.

The term "activator" refers to a compound that increases expression or activity of the PDE1A and/or PDE1C. The term thus may include small molecules, antibodies or nucleotides. In particular, the term may include small molecules and siRNAs.

By "increase the expression or activity of PDE1A and/or PDE1C" is meant to increase the level or biological activity of PDE1A and/or PDE1C relative to the level or biological activity of PDE1A and/or PDE1C in an untreated control. According to this invention, such level or activity is reduced by at least 10%, 20%, 30%, 40%, 50%, 60%, 70%, 80%, 90%, 100%, or even greater than 100%, relative to an untreated control.

As used herein, the term "activity" with respect to a PDE1A and/or PDE1C polypeptide includes any activity which is inherent to the naturally occurring PDE1A and/or PDE1C protein. In some embodiments the term "activity" refers to the degradation of cyclic nucleotides such as cAMP and cGMP. In specific embodiments, the term "activity" refers to the degradation of cGMP.

In the context of the invention the term "expression" refers to all levels of gene expression including the generation of the corresponding RNA (gene expression) as well as the generation of the corresponding protein (translation). Thus modulating the expression according to the invention may refer for example to modulating the DNA, modulating gene expression or modulating translation. Inhibiting the expression may include gene deletion, gene mutation, interfering with the process of gene expression or interfering with the process of translation.

The invention particularly refers to a PDE1A modulator and/or PDE1C modulator for use in the prevention or treatment of a medical condition.

The phrases "treatment of," "treating" and the like include the amelioration or cessation of a condition or a symptom thereof. In one embodiment, treating includes inhibiting, for example, decreasing the overall frequency of episodes of a condition or a symptom thereof.

The phrases "prevention of," "preventing" and the like include the avoidance of the onset of a condition or a symptom thereof.

A "medical condition" includes, but is not limited to, the conditions defined below.

In particular, the invention refers to a PDE1A modulator for use in the prevention or the treatment of a medical condition. In some embodiments the PDE1A is a mammalian PDE1A, preferably a human PDE1A. In the specific embodiment the compound is a selective PDE1A modulator, preferably a PDE1A inhibitor.

The invention also refers to a PDE1C modulator for use in the prevention or the treatment of a medical condition. In some embodiments the PDE1C is a mammalian PDE1C, preferably a human PDE1C. In the specific embodiment the compound is a selective PDE1C modulator, preferably a PDE1C inhibitor.

In one embodiment of the present invention, a compound of the present invention is used in the prevention or the treatment of a medical condition.

In one embodiment, the compound of the invention is a compound of the group of vincamines or a pharmaceutically acceptable derivative thereof.

In one embodiment, the compound of the present invention is a compound of Formulae (I), (II), or (III) or a pharmaceutically acceptable derivative thereof.

In one embodiment, the compound of the present invention is vinpocetin, which is used for the prevention or treatment of synucleinopathy wherein the synucleinopathy is selected from PD, PDD, MSA, DLB, PAF, RBD, or inherited synucleinopathies caused by mutations or multiplications of the α-syn gene SNCA, or synucleinopathies caused by mutations in other genes including, but not limited to GBA, LRRK2 and PARK2.

A synucleinopathy is defined by abnormal accumulation, also termed abnormal deposition, of α-syn aggregates in neurons, nerve fibers or glial cells. In particular, α-syn may be accumulated in an oligomeric form which can be detected as 37 kDa band in Western blot assays. The spectrum of synucleinopathies is for example described in Tofaris et al. (Movement Disorders, Vol. 27, No. 11, 2012, pp 1364-1369), Halliday et al. (Acta Neuropathol (2011) 122, pp 187-204), Levin et al. (Dtsch Arztebl Int 2016; 113 pp 61-9), Goedert et al. (Nat Rev Neurosci. 2001 July; 2(7) pp 492-501).

In one embodiment, the compound of the present invention is a compound of formula (I)

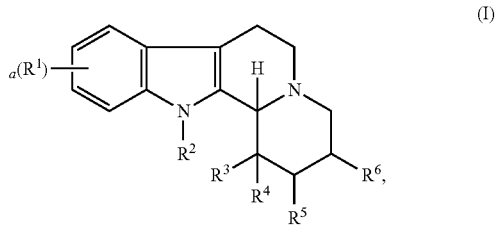

wherein
$R^1$ is selected from the group consisting of —H and halo;
a is 0, 1, 2, or 3, and preferably 0 or 1;
$R^2$ is selected from the group consisting of —H and —($C_1$-$C_6$)alkyl;

$R^3$ and $R^4$ are independently selected from the group consisting of —H, —OH, —($C_1$-$C_6$)alkyl, and —($C_1$-$C_6$)-hydroxyalkyl, or $R^3$ and $R^4$ taken together are =O, or $R^2$ and $R^3$ together with the nitrogen atom and carbon atom they are attached to form a 6-membered heterocyclic ring which is optionally substituted;

$R^5$ and $R^6$ are independently selected from the group consisting of —H and —($C_1$-$C_6$)alkyl; or $R^5$ and $R^6$ taken together form a carbon-carbon bond;

or a pharmaceutically acceptable derivative thereof;

wherein the alkyl and hydroxyalkyl groups are optionally substituted.

In one embodiment, the compound of Formula (I) is not vinpocetin. The structure of (+)-vinpocetin is shown below:

In another embodiment, $R^1$ is hydrogen.

In another embodiment, $R^1$ is halo. In a preferred aspect of this embodiment, $R^1$ is -chloro or fluoro.

In one embodiment a is 0, 1, 2, or 3 and preferably 0 or 1. In one embodiment a is 0.

In one embodiment $R^2$ is selected from the group consisting of —H and —($C_1$-$C_6$)alkyl, and preferably is hydrogen.

In one embodiment, $R^3$ is independently selected from the group consisting of —H, —OH, —($C_1$-$C_6$)alkyl, and —($C_1$-$C_6$)-hydroxyalkyl.

In another embodiment, $R^3$ is independently selected from the group consisting of —H, —OH, —($C_1$-$C_6$)alkyl, and —($C_1$-$C_6$)-hydroxyalkyl. In a preferred aspect of this embodiment $R^3$ is —H, —($C_1$-$C_6$)alkyl.

In another embodiment, $R^2$ and $R^3$ together with the nitrogen atom and carbon atom they are attached to form a 6-membered heterocyclic ring which is optionally substituted. The 6-membered heterocyclic ring is optionally substituted with 1, 2, or 3 substituents selected from the group consisting of —COOR$^7$, —OH and —($C_1$-$C_6$)alkyl. In one embodiment of this aspect, $R^7$ is selected from the group consisting of —H, —($C_1$-$C_{12}$)alkyl, —($C_2$-$C_{12}$)alkenyl, —($C_2$-$C_{12}$)alkynyl, —($C_1$-$C_{12}$)alkyl-ONO$_2$, —($C_2$-$C_{12}$)alkenyl-ONO$_2$, —($C_2$-$C_{12}$)alkynyl-ONO$_2$, (6 to 14 membered) aryl, (5 to 10 membered)heteroaryl, trimethoxyphenyl, —($C_1$-$C_6$)alkyl-(6 to 14 membered)aryl and —($C_1$-$C_6$)alkyl-(5-10 membered)heteroaryl.

In one embodiment, the compounds of formula (I) have the structure of compounds of formula (II) shown below:

In another embodiment, $R^3$ and $R^4$ in Formula (II) are independently selected from the group consisting of —H, —OH, —($C_1$-$C_6$)alkyl, and —($C_1$-$C_6$)-hydroxyalkyl.

In yet another one embodiment, $R^3$ and $R^4$ taken together are =O.

In another embodiment, $R^5$ is independently selected from the group consisting of —H and —($C_1$-$C_6$)alkyl, and preferably is —H.

In another embodiment, $R^6$ are independently selected from the group consisting of —H and —($C_1$-$C_6$)alkyl, and $R^6$ is preferably hydrogen.

In a preferred embodiment, $R^5$ and $R^6$ are both —H.

In another embodiment, $R^5$ and $R^6$ taken together form a carbon-carbon bond. In this embodiment, the compound of Formula (I) has the structure or a pharmaceutically acceptable derivative thereof.

In one embodiment, the compound of the invention is a compound of formula (II)

(II)

wherein $R^1$ is selected from the group consisting of —H and halo;

a is 0, 1, 2, or 3, and preferably 0 or 1;

$R^8$ is COOR$^7$;

$R^9$ and $R^{10}$ are independently selected from the group consisting of —H, —OH and —($C_1$-$C_6$)alkyl; or $R^9$ and $R^{10}$ taken together form a carbon-carbon bond;

$R^4$ is selected from the group consisting of —H, —OH, —($C_1$-$C_6$)alkyl, and —($C_1$-$C_6$)-hydroxyalkyl;

$R^5$ and $R^6$ are independently selected from the group consisting of —H and —($C_1$-$C_6$)alkyl, or $R^5$ and $R^6$ taken together form a carbon-carbon bond;

$R^7$ is selected from the group consisting of —H, —($C_1$-$C_{12}$)alkyl, —($C_2$-$C_{12}$)alkenyl, —($C_2$-$C_{12}$)alkynyl, —($C_1$-$C_{12}$)alkyl-ONO$_2$, —($C_2$-$C_{12}$)alkenyl-ONO$_2$, —($C_2$-$C_{12}$)alkynyl-ONO$_2$, (6 to 14 membered)aryl, (5 to 10 membered) heteroaryl, trimethoxyphenyl, —($C_1$-$C_6$)alkyl-(6 to 14 membered)aryl and —($C_1$-$C_6$)alkyl-(5 to 10 membered) heteroaryl;

or a pharmaceutically acceptable derivative thereof,

In the following, embodiment of the compounds of formula (II) are disclosed.

In one embodiment, $R^1$ is hydrogen.

In another embodiment, $R^1$ is halo. In a preferred aspect of this embodiment, $R^1$ is -chloro or fluoro.

In one embodiment a is 0, 1, 2, or 3 and preferably 0 or 1. In one embodiment a is 0.

In one embodiment, $R^4$ is selected from the group consisting of —H, —OH, —($C_1$-$C_6$)alkyl, and —($C_1$-$C_6$)-hydroxyalkyl.

In another embodiment, $R^5$ is independently selected from the group consisting of —H and —($C_1$-$C_6$)alkyl, and preferably is —H.

In another embodiment, $R^6$ are independently selected from the group consisting of —H and —($C_1$-$C_6$)alkyl, and $R^6$ is preferably hydrogen.

In a preferred embodiment, $R^5$ and $R^6$ are both —H.

In another embodiment, $R^5$ and $R^6$ taken together form a carbon-carbon bond.

$R^8$ is $COOR^7$, wherein $R^7$ is selected from the group consisting of —H, —($C_1$-$C_{12}$)alkyl, —($C_2$-$C_{12}$)alkenyl, —($C_2$-$C_{12}$)alkynyl, —($C_1$-$C_{12}$)alkyl-$ONO_2$, —($C_2$-$C_{12}$)alkenyl-$ONO_2$, —($C_2$-$C_{12}$)alkynyl-$ONO_2$, (6 to 14 membered) aryl, (5 to 10 membered)heteroaryl, trimethoxyphenyl, —($C_1$-$C_6$)alkyl-(6 to 14 membered)aryl and —($C_1$-$C_6$)alkyl-(5 to 10 membered)heteroaryl, and preferably is —H, —($C_1$-$C_{12}$)alkyl, —($C_2$-$C_{12}$)alkenyl, —($C_1$-$C_{12}$)alkynyl.

In another embodiment, $R^9$ is selected from the group consisting of —H, —OH and —($C_1$-$C_6$)alkyl. In one embodiment, $R^9$ is —H.

In another embodiment, $R^{10}$ is selected from the group consisting of —H, —OH and —($C_1$-$C_6$)alkyl. In one embodiment, $R^{10}$ is —H. In one embodiment, $R^{10}$ is —($C_1$-$C_6$)alkyl.

In yet another embodiment, $R^9$ and $R^{10}$ are both —H.

In another embodiment, $R^9$ is —H and $R^{10}$ is —($C_1$-$C_6$)alkyl

In another embodiment, $R^9$ and $R^{10}$ taken together form a carbon-carbon bond, In one embodiment of the present invention the compound of the present invention is selected from vinpocetine, apovincaminic acid, (−)-apovincaminic acid ethyl ester (CAS 68780-77-8), apovincaminic acid ethyl ester (CAS 85647-43-4), apovincaminic acid ethyl ester (CAS 77549-94-1), (−)-eburnamonine (also known as viburnine), eburnamine, dihydro-eburnamenine, apovincamine, brovincamine, vindebumol (also known as RU-24722), methylenemethoxyapovincaminate (also known as MR-711), (3S,16R)-didehydro-eburnamenine-4-methanol (also known as RGH-0537), (3S,16R)-didehydro-eburnamenine-4-methanol (also known as RGH-0537), vintoperol (also known as RGH-2981), methyl(3α,16α)-eburnamenine-14-carboxylate, methoxylenemethoxyapovincaminate, (3α,16α)-eburnamenine-14-carboxylic acid-2-(nitrooxy) ethyl ester, (14,15-dihydro-20,21-dinoreburnamenine-14-ol) (also known as vindeburnol) or a pharmaceutically acceptable derivative thereof, or further vincamine derivatives.

(−)-Apovincaminic acid ethyl ester (CAS 68780-77-8) has the following structure:

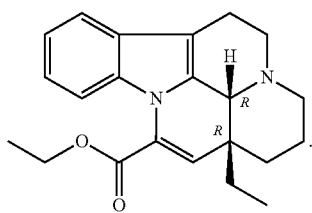

Apovincaminic acid ethyl ester (CAS 85647-43-4) has the following structure:

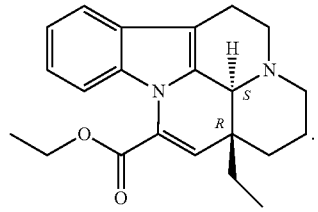

Apovincaminic acid ethyl ester (CAS 77549-94-1) has the following structure:

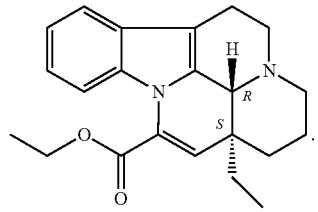

In another aspect of the present invention, compounds of formula (III) are used in the treatment of the medical condition:

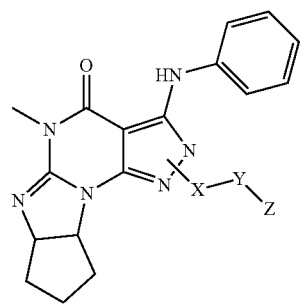

(III)

wherein
X is —($C_1$-$C_6$)alkylene;
Y is a single bond, —($C_2$-$C_{12}$)alkynylene, —($C_6$-$C_{14}$)arylene or -(5- to 10 membered)heteroarylene;
Z is —H, -(6 to 14 membered)aryl, -(5 to 10 membered)heteroaryl, halo, halo($C_1$-$C_6$)alkyl-, —C(O)—$R^1$, —N($R^2$)($R^3$), or —($C_3$-$C_7$)cycloalkyl, wherein the —($C_3$-$C_7$)cycloalkyl optionally comprises at least one heteroatom selected from a group consisting of N or O;
$R^1$ is —($C_1$-$C_6$)alkyl, halo($C_1$-$C_6$)alkyl;
$R^2$ and $R^3$ are independently selected from H or —($C_1$-$C_6$)alkyl,
wherein X, Y and Z are independently and optionally substituted with halo,
or a pharmaceutically acceptable derivative thereof.

In one embodiment, X is selected from -methylene, ethylene, propylene, butylene, pentylene or hexylene. In another embodiment, X is selected from -methylene, ethylene, propylene, or butylene. In another embodiment, X is -methylene or ethylene. In yet another embodiment, X is -methylene. In one embodiment, the X group is optionally substituted.

In one embodiment, Y is selected from a single bond, —($C_2$-$C_{12}$)alkenylene, —($C_2$-$C_{12}$)alkynylene, —($C_6$-$C_{14}$)arylene or —($C_5$-$C_{10}$)heteroarylene. In another embodiment, Y is selected from a single bond, —($C_6$-$C_{14}$)arylene or —($C_5$-$C_{10}$)heteroarylene. In one embodiment, Y is —($C_6$-$C_{14}$)arylene. In one embodiment, the Y group is optionally substituted. In another embodiment, the —($C_6$-$C_{14}$)arylene or —($C_5$-$C_{10}$)heteroarylene are optionally substituted.

In one embodiment, the Z group is selected from —H, -(6 to 14 membered)aryl, -(5 to 10 membered)heteroaryl, halo, halo($C_1$-$C_6$)alkyl-, —C(O)—$R^1$, —N($R^2$)($R^3$), or —($C_3$-$C_7$)cycloalkyl, wherein the —($C_3$-$C_7$)cycloalkyl optionally comprises at least one heteroatom selected from a group consisting of N or O. In another embodiment, the Z group is optionally substituted.

In another embodiment, the Z group is selected from -(6 to 14 membered)aryl, -(5 to 10 membered)heteroaryl, which are optionally substituted. In another embodiment, the Z group is selected from -(5 to 10 membered)heteroaryl, which are optionally substituted by 1, 2, or 3 halo.

In one embodiment, the Z-group is —($C_3$-$C_7$)cycloalkyl, wherein the —($C_3$-$C_7$)cycloalkyl optionally comprises at least one heteroatom selected from a group consisting of N or O. In one embodiment, Z is —($C_3$-$C_7$)cycloalkyl, wherein the —($C_3$-$C_7$)cycloalkyl is selected from cyclopropyl, cyclobutyl, cyclopentyl, cyclohexyl or cycloheptyl. The —($C_3$-$C_7$)cycloalkyl group may optionally be substituted.

In another embodiment, the Z-group is —($C_3$-$C_7$)cycloalkyl, wherein the —($C_3$-$C_7$)cycloalkyl comprises at least one heteroatom selected from a group consisting of N or O. In case the —($C_3$-$C_7$)cycloalkyl comprises an oxygen atom, the Z group includes an oxiran group, an oxetan group, a tetrahydrofuran, or a tetrahydropyran group. In case the —($C_3$-$C_7$)cycloalkyl comprises a nitrogen atom, the Z group includes a azetan, a pyrrolidin or a piperidine. In case, a nitrogen and an oxygen atom are comprised in the —($C_3$-$C_7$)cycloalkyl group, the Z group includes e.g. morpholino. In case the —($C_3$-$C_7$)cycloalkyl comprises a nitrogen atom, the group may be attached either via a carbon or the nitrogen atom.

In one embodiment, Z is —C(O)—$R^1$. In one aspect of this embodiment, $R^1$ is —($C_1$-$C_6$)alkyl or halo($C_1$-$C_6$)alkyl and is preferably $R^1$ is —($C_1$-$C_6$)alkyl.

In one embodiment of a compound of formula (III), Z is —N($R^2$)($R^3$). In one aspect of this embodiment, $R^2$ and $R^3$ are independently selected from H or —($C_1$-$C_6$)alkyl, wherein the alkyl group is optionally substituted. In another embodiment, Z is —N(H)($C_1$-$C_6$)alkyl. In another embodiment, Z is —N(($C_1$-$C_6$)alkyl)$_2$.

In one embodiment, the compound of formula (III) has the following structure:

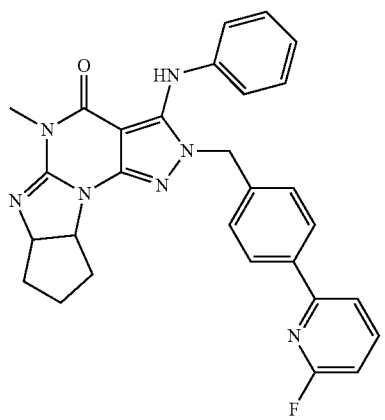 [SMILES: CN1C(=O)c2c(nn(Cc3ccc(-c4cccc(F)n4)cc3)c2Nc2ccccc2)N2C1=NC1CCCC12]

or a pharmaceutically acceptable derivative thereof.

In one embodiment, the compound of formula (III) is (6aR,9aS)-2-(4-(6-fluoropyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4-(2H)-one or a pharmaceutically acceptable derivative thereof such as the phosphate salt. This compound has also been described as ITI-214 in the art.

In another embodiment, the compound of the present invention is 8-methoxymethyl-3-isobutyl-1-methylxanthine (8MM-IBMX), compound IC86340 (from ICOS), compound IC295 (ICOS/Eli Lilly).

In one embodiment, the pharmaceutically acceptable derivative is a pharmaceutically acceptable salt or solvate there.

As used in connection with the Compounds of the present invention having the formulae (I), (II), or (III) herein, the terms used herein having following meaning:

"—($C_1$-$C_{12}$)alkyl" means a straight chain or branched non-cyclic hydrocarbon having from 1 to 12 (i.e. 1, 2, 3, 4, 5, 6, 7, 8, 9, 10, 11, or 12) carbon atoms. Representative straight chain —($C_1$-$C_{12}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —($C_1$-$C_{10}$)alkyl groups, such as methyl, ethyl or propyl, replace one or both hydrogens in a —$CH_2$— group of a straight chain alkyl. A branched non-cyclic hydrocarbon means that one or more straight chain —($C_1$-$C_{12}$)alkyl groups, such as methyl, ethyl or propyl, replace one or both hydrogens in a —$CH_2$— group of a straight chain non-cyclic hydrocarbon. Representative branched —($C_1$-$C_{12}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—($C_1$-$C_4$)alkyl" means a straight chain or branched non-cyclic hydrocarbon having from 1 to 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"—($C_2$-$C_{12}$)alkenyl" means a straight chain or branched non-cyclic hydrocarbon having from 2 to 12 carbon atoms and including at least one carbon-carbon double bond. A branched alkenyl means that one or more straight chain —($C_1$-$C_{10}$)alkyl groups, such as methyl, ethyl or propyl, replace one or both hydrogens in a —$CH_2$— or —CH= group of a straight chain alkenyl. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like. In some embodiments the "—($C_2$-$C_{12}$)alkenyl" groups are "—($C_2$-$C_6$)alkenyl" groups.

"—($C_2$-$C_{12}$)alkynyl" means a straight chain or branched non-cyclic hydrocarbon having from 2 to 12 carbon atoms and including at least one carbon-carbon triple bond. A branched alkynyl means that one or more straight chain —(C$_1$-C$_{10}$)alkyl groups, such as methyl, ethyl or propyl, replace one or both hydrogens in a —CH$_2$— group of a straight chain alkynyl. Representative straight chain and branched —(C$_2$-C$_{12}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—(C$_3$-C$_7$)cycloalkyl" means a saturated monocyclic hydrocarbon having from 3 to 7 carbon atoms. Representative (C$_3$-C$_7$)cycloalkyls are -cyclopropyl, -cyclobutyl, -cyclopentyl, -cyclohexyl, -cycloheptyl.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(6-membered)heterocycle" or "-(6-membered)heterocyclo" means a 6-membered monocyclic heterocyclic ring which is either saturated, unsaturated non-aromatic, or aromatic. A 6-membered heterocycle can contain up to 4 heteroatoms. Each heteroatom is independently selected from nitrogen, which can be quaternized; oxygen; and sulfur, including sulfoxide and sulfone. The -(6-membered)heterocycle can be attached via a nitrogen or carbon atom. Representative -(6-membered)heterocycles include pyridyl, thiophenyl, pyridazinyl, pyrimidinyl, triazinyl, morpholinyl, pyrrolidinonyl, pyrrolidinyl, piperidinyl, piperazinyl, dihydropyridinyl, tetrahydropyridinyl, tetrahydropyrimidinyl, tetrahydrothiophenyl, tetrahydrothiopyranyl, and the like.

In the context of the Compound of Formula (I) and the option that R$^2$ and R$^3$ form together with the nitrogen and carbon atom they are attached to a -(6-membered)heterocycle, the compound of Formula (I) may have the following structure:

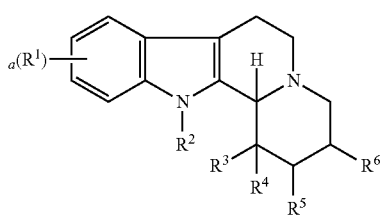

(I)

"—(C6 to C14)aryl" means a 6 to 14-membered aromatic carbocyclic moiety such as -phenyl, anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl. A preferred embodiment of the "-(5- to 10-membered)heteroaryl" is a "-(5- or 6-membered)heteroaryl".

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"(halo)(C$_1$-C$_6$)alkyl" means a (C$_1$-C$_6$)alkyl group as defined above wherein one or more (e.g. 1, 2, 3, or 4) of the hydrogens of the alkyl group has been replaced with a halogen.

"(hydroxy)(C$_1$-C$_6$)alkyl" means a (C$_1$-C$_6$)alkyl group as defined above wherein one or more (e.g. 1, 2, 3, or 4) of the hydrogens of the alkyl group have been replaced with a —OH group.

Representative (halo)(C$_1$-C$_6$)alkyl groups include —CF$_2$CF$_3$, —CF$_3$, —CCl$_3$, —CBr$_3$, and —Cl$_3$.

"-Halogen" or "-halo" means —F, —Cl, —Br, or —I.

"Oxo", "=O", and the like as used herein mean an oxygen atom doubly bonded to carbon or another element.

"Amino" means —NH$_2$.

"Carboxy" means —COOH.

"Nitro" means NO$_2$.

"Cyano" means —CN.

"Carbonyl" means C(O).

As used herein, the term "optionally substituted" refers to a group that may be unsubstituted or substituted.

Optional substituents on optionally substituted groups, when not otherwise indicated, include one or more groups, preferably 1, 2, or 3 groups, independently selected from the group consisting of halo, halo(C$_{1-6}$)alkyl, -(6 to 14 membered)aryl, heterocycle, —(C$_3$-C$_7$)cycloalkyl, —(C$_1$-C$_6$)alkyl, (C$_1$-C$_{10}$)alkenyl, (C$_1$-C$_{10}$)alkynyl, -(6 to 14 membered)aryl(C$_{1-6}$)alkyl, -(6 to 14 membered)aryl(C$_{2-6}$)alkenyl, -(6 to 14 membered)aryl(C$_{2-6}$)alkynyl, —(C$_3$-C$_7$)cycloalkyl(C$_{1-6}$) alkyl, heterocyclo(C$_{1-6}$)alkyl, hydroxy(C$_{1-6}$)alkyl, amino (C$_{1-6}$)alkyl, carboxy(C$_{1-6}$)alkyl, nitro, amino, cyano, alkylcarbonylamino, hydroxy, groups mentioned above.

Preferred optional substituents include halo, halo($C_{1-6}$)alkyl, hydroxy($C_{1-6}$)alkyl, amino($C_{1-6}$)alkyl, hydroxy, nitro, ($C_{1-6}$)alkyl, and amino.

The phrase "pharmaceutically acceptable derivative", as used herein, includes any pharmaceutically acceptable salt, polymorph, pseudopolymorph, solvate, prodrug, radiolabeled form, stereoisomer, enantiomer, diastereomer, other stereoisomeric form, racemic mixture, geometric isomer, and/or tautomer, e.g., of a Compound of the present invention.

In one embodiment, the pharmaceutically acceptable derivative is a pharmaceutically acceptable salt, e.g., of a Compound of present invention. In another embodiment, the pharmaceutically acceptable derivative is a polymorph, e.g., of a Compound of the present invention. In another embodiment, the pharmaceutically acceptable derivative is a pseudopolymorph, e.g., of a Compound of the present invention. In another embodiment, the pharmaceutically acceptable derivative is a solvate, e.g., of a Compound of the present invention. In another embodiment, the pharmaceutically acceptable derivative is a prodrug, e.g., of a Compound of the present invention. In another embodiment, the pharmaceutically acceptable derivative is a radiolabeled form, e.g., of a Compound the present invention. In another embodiment, the pharmaceutically acceptable derivative is a stereoisomer, e.g., of a Compound of the present invention. In another embodiment, the pharmaceutically acceptable derivative is an enantiomer, e.g., of a Compound of the present invention. In another embodiment, the pharmaceutically acceptable derivative is a diastereomer, e.g., of a Compound of the present invention. In another embodiment, the pharmaceutically acceptable derivative is a stereoisomeric form other than a stereoisomer, an enantiomer and a diastereomer, e.g., of a Compound of the present invention. In another embodiment, the pharmaceutically acceptable derivative is a racemic mixture, e.g., of a Compound of the present invention. In another embodiment, the pharmaceutically acceptable derivative is a geometric isomer, e.g., of a Compound of the present invention. In another embodiment, the pharmaceutically acceptable derivative is a tautomer, e.g., of a Compound of the present invention.

The phrase "pharmaceutically acceptable salt", as used herein, is any pharmaceutically acceptable salt that can be prepared from a Compound of the present invention including a salt formed from an acid and a basic functional group, such as a nitrogen group, of a Compound of the present invention. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Compound of the present invention having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl) amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. One skilled in the art will recognize that, e.g., acid addition salts, of a Compound of the present invention can be prepared by reaction of the compounds with the appropriate acid by a variety of known methods.

The compounds of the present invention provided herein also encompass all polymorphs and pseudopolymorphs of the Compounds of the present invention. "Polymorphs" are known in the art (see, e.g., Giron, "Investigations of Polymorphism and Pseudo-polymorphism in Pharmaceuticals by Combined Thermoanalytical Techniques," *J. Thermal Anal. Cal.* 64:37-60 (2001)) and are considered to be different crystalline phases in which a Compound of Formula (I) is capable of existing. The crystalline phases can have different arrangements ("packing polymorphism") and/or conformations ("conformational polymorphism") of the molecules in the crystal lattice. For example, in two distinct polymorphs of a Compound of the present invention, each polymorph can have the molecules arranged in a different fundamental crystal system—triclinic, monoclinic, orthorhombic, tetragonal, trigonal, hexagonal, or cubic. The term "anhydrate" as used herein, is any crystalline form of a Compound of the present invention in which water molecules are a non-integral part of the crystal. An anhydrate of a Compound of the present invention can be prepared, for example, by crystallization from a solvent substantially free of water. In one embodiment, the Compound of the present invention is present as an anhydrate, i.e., as a free base where the crystal lattice is substantially free of water molecules and any water molecules present are present as "surface water" (e.g., loosely bound to the crystal's surface) as would be discernable and distinguishable to those in the art by, e.g., thermogravimetric analysis (TGA) and/or differential scanning calorimetry (DSC), from water molecules that are an integral part of the crystal (e.g., a hydrate). An anhydrate of a Compound of the present invention has less than about 0.2 mole water in one embodiment, less than about 0.15 mole water in another embodiment, less than about 0.12 mole water in another embodiment, less than about 0.1 mole water in another embodiment, less than about 0.085 mole water in another embodiment, less than about 0.075 mole water in another embodiment, less than about 0.06 mole water in another embodiment, less than about 0.057 mole water in another embodiment, less than about 0.05 mole water in another embodiment, less than about 0.03 mole water in another embodiment, less than about 0.025 mole water in another embodiment, less than about 0.02 mole water in another embodiment, less than about 0.01 mole water in another embodiment, less than about 0.005 mole water in another embodiment, and less than about 0.001 mole water in another embodiment, each said embodiment taking into account the presence of surface water and each said embodiment being per 1 mole of a Compound of the present invention.

The compounds of the disclosure provided herein also encompass all solvates of the Compounds of the present invention. "Solvates" are known in the art and are considered to be a combination, physical association and/or solvation of a Compound of the present invention with a solvent molecule. This physical association can involve varying degrees of ionic and covalent bonding, including hydrogen bonding. When the solvate is of the stoichiometric type, there is a fixed ratio of the solvent molecule to Compound of the present invention, e.g., a disolvate, monosolvate or hemisolvate when the solvent molecule:Compound of the present invention molecule molar ratio is 2:1, 1:1 or 1:2, respectively. In other embodiments, the solvate is of the nonstoichiometric type. For example, the Compound of the present invention crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. As the crystalline form of a solvate can also be referred to as a "pseudopolymorph", the compounds of the disclosure provided herein also encompass all pseudopolymorphs of the Compounds of the present invention. A Compound of the present invention of the disclosure can be present as a solvated form with a pharmaceutically acceptable solvent, such as water, methanol, ethanol, and the like, and it is intended that the disclosure include both solvated and unsolvated Compound of the present invention forms. As "hydrate" relates to a particular subgroup of solvates, i.e., where the solvent molecule is water, hydrates are included within the solvates of the disclosure. In one embodiment, the Compound of the present invention is present as a monohydrate, i.e., as a free base where the water:Compound of the present invention molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.,* 93(3): 601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.,* 5(1):Article 12 (2004), and Bingham et al., "Over one hundred solvates of sulfathiazole," *Chem. Comm.,* pp. 603-604 (2001). In one embodiment, a non-limiting, process involves dissolving the Compound of the present invention in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The compounds disclosed herein also comprise all prodrugs of the Compounds of the present invention. "Prodrugs" are known in the art and, while not necessarily possessing any pharmaceutical activity as such, are considered to be any covalently bonded carrier(s) that releases the active parent drug in vivo. In general, such prodrugs will be a functional derivative of a Compound of the present invention which is readily convertible in vivo, e.g., by being metabolized, into the required Compound of the present invention. Conventional procedures for the selection and preparation of suitable prodrug derivatives are described in, for example, H. Bundgaard ed., *Design of Prodrugs,* Elsevier (1985); "Drug and Enzyme Targeting, Part A," Widder et al., eds., Vol. 112 in *Methods in Enzymology,* Academic Press (1985); Bundgaard, "Design and Application of Prodrugs," Chapter 5, pp. 113-191 in *A Textbook of Drug Design and Development,* Krogsgaard-Larsen and Bundgaard Eds., Harwood Academic Publishers (1991); Bundgaard et al., "(C) Means to Enhance Penetration (1) Prodrugs as a means to improve the delivery of peptide drugs," *Adv. Drug Delivery Revs.* 8:1-38 (1992); Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988); and Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).

In addition, one or more hydrogen, carbon or other atoms of a Compound of the present invention can be replaced by a radioactive isotope of the hydrogen, carbon or other atoms. Such a "radiolabeled", "radiolabeled form", and the like of a Compound of the present invention, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Compound of the present invention of the disclosure include isotopes of hydrogen, carbon, nitrogen, oxygen, phosphorous, sulfur, fluorine, chlorine, bromine, and iodine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$, respectively. In one embodiment, a radiolabeled Compound of the present invention contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Compound of the present invention contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Compound of the present invention contains 1 radioactive isotope which is selected from hydrogen, carbon, nitrogen, oxygen, phosphorous, sulfur, fluorine, chlorine, bromine, and iodine. In another embodiment, a radiolabeled Compound of the present invention contains 1, 2, 3, 4, or more radioactive isotopes, each of which is independently selected from $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Compound of the present invention contains 1 or 2 radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, 81Br, $^{123}$I, $^{124}$I, $^{125}$I, and $^{131}$I. In another embodiment, a radiolabeled Compound of the present invention contains 1 radioactive isotope which is selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Compound of the present invention contains 1, 2, 3, 4, or more radioactive isotopes, each of which is independently selected from $^2$H, $^3$H, $^{13}$C, $^{14}$C, $^{15}$N, $^{18}$O, $^{32}$P, and $^{125}$I. In another embodiment, a radiolabeled Compound of the present invention contains 1 or 2 radioactive isotopes, each of which is independently selected from $^3$H, $^{14}$C, $^{15}$N, $^{18}$O, $^{32}$P, and $^{125}$I. In another embodiment, a radiolabeled Compound of the present invention contains 1 radioactive isotope which is selected from $^3$H, $^{14}$C, $^{15}$N, $^{18}$O, $^{32}$P, and $^{125}$I.

Radiolabeled compounds of the disclosure can be prepared by methods known in the art. For example, tritiated Compounds of the present invention can be prepared by introducing tritium into the particular Compound of the present invention, for example, by catalytic dehalogenation with tritium. This method can include reacting a suitably halogen-substituted precursor of a Compound of the present invention with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," Chapter 6, pp. 155-192 in *Isotopes in the Physical and Biomedical Sciences, Vol. 1, Labeled Compounds (Part A)* (1987). $^{14}$C-labeled compounds can be prepared by employing starting materials having a $^{14}$C carbon. Compounds containing piperazine isotopically enriched with $^{13}$C and/or $^{15}$N can be prepared as described in, e.g., FIG. 5A and the associated description, of U.S. Pat. No. 7,355,045 B2.

A Compound of the present invention can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. When a Compound of the present invention contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., ketone-enol, amide-imidic acid, lactam-lactim, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Compound of the present invention can be obtained by known techniques such as chiral chromatography or formation of diastereomeric salts from an optically active acid or base.

Therapeutic/Prophylactic Administration and Compositions of the Disclosure

In one embodiment of the invention, the compounds of the present invention such as compounds of formula (I); (II), or (III) or pharmaceutically acceptable derivatives thereof are used in the prevention and/or treatment of a medical condition. In one embodiment, the medical condition is a synucleinopathy. In one embodiment, the compounds of formula (I); (II), or (III) or pharmaceutically acceptable derivatives thereof are used in the prevention and/or treatment of a synucleinopathy, wherein the synucleinopathy is selected from PD, PDD, MSA, DLB, PAF, RBD, or inherited synucleinopathies caused by mutations or multiplications of the α-syn gene SNCA, or synucleinopathies caused by mutations in other genes including, but not limited to GBA, LRRK2 and PARK2.

In one aspect of the present invention, Vinpocetine or a pharmaceutically acceptable derivative thereof is used in the treatment of a synucleinopathy selected from the group consisting of PD, MSA, DLB, PAF, RBD, and inherited synucleinopathies caused by mutations or multiplications of the α-syn gene SNCA, or synucleinopathies caused by mutations in other genes including, but not limited to GBA, LRRK2 and PARK2. In one aspect of this embodiment, MSA is selected from MSA with predominantly cerebellar symptoms (MSA-C) or MSA with predominantly parkinsonian symptoms (MSA-P).

Another embodiment the invention refers to a nucleic acid for use according to the invention. In one embodiment the compound is RNA. In a specific embodiment the RNA is single-stranded or double-stranded RNA. The RNA may be selected from the group consisting of viral RNA, retroviral RNA, small interfering RNA (siRNA), antisense RNA, aptamers, microRNA (miRNA), double-stranded RNA (dsRNA), small hairpin RNA (shRNA), and Piwi-interacting RNA (piRNA). Preferably, the RNA is selected from the group consisting of siRNA, antisense RNA, dsRNA, and shRNA, more preferably siRNA.

In a specific embodiment of the invention the RNA comprises or consists of a nucleotide sequence which exhibits at least 50%, at least 60%, at least 70%, at least 80%, at least 85%, at least 90%, at least 95%, at least 96%, at least 97%, at least 98%, or at least 99% identity to the sequence according to SEQ ID NO: 1 and/or SEQ ID NO: 3. In a more specific embodiment of the invention, the RNA comprises or consists of a nucleotide sequence of SEQ ID NO: 1 and/or SEQ ID NO: 3. Typically, the nucleic acid is a synthetic nucleic acid. The nucleic acid may be an isolated nucleic acid.

"RNA" is the usual abbreviation for ribonucleic acid. Usually RNA may be obtainable by transcription of a DNA-sequence, e.g., inside a cell. The term "RNA" further encompass other coding RNA molecules, such as viral RNA, retroviral RNA and replicon RNA, small interfering RNA (siRNA), microRNA (miRNA), double-stranded RNA (dsRNA), small hairpin RNA (shRNA), antisense RNA (asRNA), CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

"viral RNA" is RNA derived from a virus, for example a retrovirus. It may be directly translated into the desired viral proteins. Portions of the viral RNA may be skipped during translation. The result is that many different proteins can be created from the same mRNA strand, with similar 5' ends (to varying degrees) and same 3' ends. Or, different proteins can be created from positive sense viral RNA and negative sense viral RNA.

A "replicon" is an RNA molecule, or a region of an RNA, that replicates from a single origin of replication.

"Antisense RNA" (asRNA) or 2mRNA-interfering complementary RNA" (micRNA) is a single-stranded RNA that is complementary to a portion of an mRNA strand transcribed within a cell. Antisense RNA may for example be introduced into a cell to inhibit translation of a complementary mRNA by base pairing to it and physically obstructing the translation machinery.

"Small interfering RNA (siRNA)", also known as short interfering RNA or silencing RNA, is a class of double-stranded RNA molecules, 20-25 base pairs in length. siRNA plays many roles, but it is most notable in the RNA interference (RNAi) pathway, where it interferes with the expression of specific genes with complementary nucleotide sequences. siRNA functions by causing mRNA to be broken down after transcription, resulting in no translation. siRNA also acts in RNAi-related pathways, e.g., as an antiviral mechanism or in shaping the chromatin structure of a genome. siRNAs have a well-defined structure: a short (usually 20 to 24-bp) double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs.

"Ribozymes" are ribonucleic acid enzymes, also termed catalytic RNA. Ribozymes are RNA molecules that are capable of catalyzing specific biochemical reactions, similar to the action of protein enzymes. Ribozymes have diverse structures and mechanisms. Examples of ribozymes include the hammerhead ribozyme, the VS ribozyme, Leadzyme and the hairpin ribozyme.

"Aptamers" (from the Latin aptus—fit, and Greek meros—part) are RNA-based oligonucleotide molecules that bind to a specific target molecule. Aptamers are usually created by selecting them from a large random sequence pool, but natural aptamers also exist in riboswitches. Aptamers also include RNA-based oligonucleotide molecules that bind to a specific target molecule that are combined with ribozymes to self-cleave in the presence of their target molecule.

"CRISPR (clustered regularly interspaced short palindromic repeats)" refer to segments of prokaryotic DNA containing short repetitions of base sequences. Each repetition is followed by short segments of "spacer DNA" from previous exposures to a bacterial virus or plasmid. CRISPRs are found in approximately 40% of sequenced bacteria genomes and 90% of sequenced archaea. CRISPRs are often associated with cas genes that code proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms.

"Piwi-interacting RNA" (piRNA) is the largest class of small non-coding RNA molecules expressed in animal cells. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. piRNAs have been identified in both vertebrates and invertebrates, and although biogenesis and modes of action do vary somewhat between species, a number of features are conserved. piRNAs have no clear secondary structure motifs, the length of a piRNA is between 26 and 31 nucleotides, and the bias for a 5' uridine is common to piRNAs in both vertebrates and invertebrates. piRNAs are found in clusters throughout the genome; these clusters may contain as few as ten or up to many thousands of piRNAs and can vary in size from one to one hundred kb.

In one embodiment of the invention the medical condition is a synucleinopathy. The synucleinopathy may be selected from Parkinson's disease (PD), Parkinson's disease with dementia (PDD), multiple system atrophy (MSA), dementia with Lewy bodies (DLB), pure autonomic failure (PAF), rapid eye movement sleep behavior disorder (RBD), or inherited synucleinopathies caused by mutations or multiplications of the α-syn gene SNCA, or synucleinopathies caused by mutations in other genes including, but not limited to GBA, LRRK2 and PARK2.

Preferably the synucleinopathy is PDD, MSA, DLB, PAF, RBD. More preferably the synucleinopathy is MSA or RBD. In one embodiment the synucleinopathy is MSA. The multiple system atrophy (MSA) is selected from MSA with predominantly cerebellar symptoms (MSA-C) or MSA with predominantly parkinsonian symptoms (MSA-P).

In one embodiment, the synucleinopathy is rapid eye movement sleep behavior disorder (RBD).

In one embodiment, the synucleinopathy is RBD, without tremor. In one embodiment, the synucleinopathy is RBD without bradykinesia, rigidity, tremor and postural instability. In one embodiment, the synucleinopathy is RBD wherein no symptoms of Parkinson's disease are present.

Due to their activity, Compounds of the present invention, or a pharmaceutically acceptable derivative thereof, are advantageously useful in veterinary and human medicine. As described above, compounds of the present invention, or a pharmaceutically acceptable derivative thereof, are useful for treating or preventing a condition.

When administered to an animal, compounds of the present invention, or a pharmaceutically acceptable derivative thereof, are, in one embodiment, administered as a component of a composition that comprises a pharmaceutically acceptable carrier or excipient. The compositions, which comprise a Compound of the present invention, or a pharmaceutically acceptable derivative thereof, can be administered orally. The compounds of the invention, or a pharmaceutically acceptable derivative thereof, can also be administered by any other convenient route, for example, by infusion or bolus injection, by absorption through epithelial or mucocutaneous linings (e.g., oral, rectal, and intestinal mucosa, etc.) and can be administered together with another therapeutically active agent. Administration can be systemic or local. Various delivery systems are known, e.g., encapsulation in liposomes, microparticles, microcapsules, capsules, etc., and can be used to administer the Compound of the present invention, or a pharmaceutically acceptable derivative thereof.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of Compounds of the present invention, or a pharmaceutically acceptable derivative thereof, into the bloodstream.

In specific embodiments, it can be desirable to administer the Compounds of the present invention, or a pharmaceutically acceptable derivative thereof, locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Compounds of the present invention or a pharmaceutically acceptable derivative thereof, into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of the present invention can be formulated as a suppository, with traditional binders and excipients such as triglycerides.

In another embodiment, the Compounds of the present invention, or a pharmaceutically acceptable derivative thereof, can be delivered in a vesicle, in particular a liposome (see Langer, "New Methods of Drug Delivery," Science 249:1527-1533 (1990); Lopez-Berestein, "Treatment of Systemic Fungal Infections with Liposomal-Amphotericin B," Liposomes in the Therapy of Infectious Disease and Cancer, pp. 317-327 (1989); and Treat et al., "Liposome encapsulated doxorubicin—preliminary results of phase I and phase II trials" Liposomes in the Therapy of Infectious Disease and Cancer, pp. 353-365 (1989).

In yet another embodiment, the Compounds of the present invention, or a pharmaceutically acceptable derivative thereof, can be delivered in a controlled-release system or sustained-release system (see, e.g., Goodson, "Dental Applications," pp. 115-138 in Medical Applications of Controlled Release, Vol. 2, Applications and Evaluation, Langer and Wise, eds., CRC Press (1984), hereafter "Goodson"). Other controlled- or sustained-release systems discussed in the review by Langer, Science 249:1527-1533 (1990) can be used. In one embodiment, a pump can be used (Langer, Science 249:1527-1533 (1990); Sefton, "Implantable Pumps," in CRC Crit. Rev. Biomed. Eng. 14(3):201-240 (1987); Buchwald et al., "Long-term, Continuous Intravenous Heparin Administration by an Implantable Infusion Pump in Ambulatory Patients with Recurrent Venous Thrombosis," Surgery 88:507-516 (1980); and Saudek et al., "A Preliminary Trial of the Programmable Implantable Medication System for Insulin Delivery," New Engl. J. Med. 321:574-579 (1989)). In another embodiment, polymeric materials can be used (see Goodson; Smolen et al., "Drug Product Design and Performance," Controlled Drug Bioavailability Vol. 1, John Wiley & Sons, New York (1984); Langer et al., "Chemical and Physical Structure of Polymers as Carriers for Controlled Release of Bioactive Agents: A Review," J. Macromol. Sci. Rev. Macromol. Chem. C23(1): 61-126 (1983); Levy et al., "Inhibition of Calcification of Bioprosthetic Heart Valves by Local Controlled-Release Diphosphonate," Science 228:190-192 (1985); During et al., "Controlled Release of Dopamine from a Polymeric Brain Implant: In Vivo Characterization," Ann. Neurol. 25:351-356 (1989); and Howard et al., "Intracerebral drug delivery in rats with lesion-induced memory deficits," J. Neurosurg. 71:105 (1989)). In yet another embodiment, a controlled- or sustained-release system can be placed in proximity of a target of the Compounds of the present invention, e.g., the spinal column, brain, or gastrointestinal tract, thus requiring only a fraction of the systemic dose.

The compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the present invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, (Amer. Pharmaceutical Ass'n, Washington, D.C., 1986), incorporated herein by reference.

The compositions can take the form of solutions, suspensions, emulsion, tablets, pills, pellets, multiparticulates, capsules, capsules containing liquids, powders, sustained release formulations, suppositories, emulsions, aerosols, sprays, suspensions, or any other form suitable for use. In one embodiment, the composition is in the form of a capsule (see e.g., U.S. Pat. No. 5,698,155). Other examples of suitable pharmaceutical excipients are described by Radebough et al., "Preformulation," pp. 1447-1676 in Remington's Pharmaceutical Sciences Vol. 2 (Gennaro, ed., 19th ed., Mack Publishing, Easton, Pa., 1995), incorporated herein by reference.

In one embodiment, the Compounds of the present invention are formulated in accordance with routine procedures as a composition adapted for oral administration to human beings. A Compound of the present invention to be orally delivered can be in the form of tablets, capsules, gelcaps, caplets, lozenges, aqueous or oily solutions, suspensions, granules, powders, emulsions, syrups, or elixirs, for example. When a Compound of the present invention is incorporated into oral tablets, such tablets can be compressed, tablet triturates, enteric-coated, sugar-coated, film-coated, multiply compressed or multiply layered. Techniques and compositions for making solid oral dosage forms are described in Pharmaceutical Dosage Forms: Tablets (Lieberman et al., eds., 2nd ed., Marcel Dekker, Inc., 1989

& 1990). Techniques and compositions for making tablets (compressed and molded), capsules (hard and soft gelatin) and pills are also described by King, "Tablets, Capsules, and Pills," pp. 1553-1593 in Remington's Pharmaceutical Sciences (Osol, ed., 16th ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in Pharmaceutical Dosage Forms: Disperse Systems (Lieberman et al., eds., 2nd ed., Marcel Dekker, Inc., 1996 & 1998).

When a Compound of Formula (I) is to be injected parenterally, it can be, e.g. in the form of an isotonic sterile solution. Alternatively, when a Compound of the present invention is to be inhaled, it can be formulated into a dry aerosol or can be formulated into an aqueous or partially aqueous solution.

An orally administered Compound of the present invention can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Compounds of the present invention can be formulated for intravenous administration. In one embodiment, compositions for intravenous administration comprise sterile isotonic aqueous buffer. Where necessary, the compositions can also include a solubilizing agent. A Compound of the present invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the present invention is to be administered by infusion, it can be dispensed, for example, with an infusion bottle containing sterile pharmaceutical grade water or saline. Where a Compound of the present invention is administered by injection, an ampule of sterile water for injection or saline can be provided so that the ingredients can be mixed prior to administration.

The Compounds of the present invention, or a pharmaceutically acceptable derivative thereof, can be administered by controlled-release or sustained-release means or by delivery devices that are known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled or sustained-release of one or more active ingredients using, for example, hydropropylmethyl cellulose, ethylcellulose, other polymer matrices, gels, permeable membranes, osmotic systems, multilayer coatings, microparticles, liposomes, microspheres, or a combination thereof to provide the desired release profile in varying proportions. Suitable controlled or sustained-release formulations known to those of ordinary skill in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled or sustained-release.

Controlled- or sustained-release pharmaceutical compositions can have a common goal of improving drug therapy over that achieved by their non-controlled or non-sustained release counterparts. In one embodiment, a controlled- or sustained-release composition comprises a minimal amount of a Compound of the present invention to cure or control the condition in a minimum amount of time. Advantages of controlled or sustained-release compositions include extended activity of the drug, reduced dosage frequency, and increased patient compliance. In addition, controlled or sustained-release compositions can favorably affect the time of onset of action or other characteristics, such as blood levels of the Compound of the present invention, and can thus reduce the occurrence of adverse side effects.

Controlled- or sustained-release compositions can be designed to immediately release an amount of a Compound of the present invention, or a pharmaceutically acceptable derivative thereof, that promptly produces the desired therapeutic or prophylactic effect, and gradually and continually release other amounts of the Compound of the present invention to maintain this level of therapeutic or prophylactic effect over an extended period of time. To maintain a constant level of the Compound of the present invention in the body, the Compound of the present invention can be released from the dosage form at a rate that will replace the amount of Compound of the present invention being metabolized and excreted from the body. Controlled or sustained-release of an active ingredient can be stimulated by various conditions, including but not limited to, changes in pH, changes in temperature, concentration or availability of enzymes, concentration or availability of water, or other physiological conditions or compounds.

The amount of the Compound of the present invention, or a pharmaceutically acceptable derivative thereof that is effective in the treatment or prevention of a Condition can be determined by standard clinical techniques. In addition, in vitro or in vivo assays can optionally be employed to help identify optimal dosage ranges. The precise dose to be employed will also depend on the route of administration, and the seriousness of the Condition and can be decided according to the judgment of a practitioner and/or each animal's circumstances. Suitable effective dosage amounts, however, will, in one embodiment, range from about 0.005 mg/kg of body weight to about 2500 mg/kg of body weight, in another embodiment, range from about 0.01 mg/kg of body weight to about 2500 mg/kg of body weight, although they are, in another embodiment, about 100 mg/kg of body weight or less. In one embodiment, the effective dosage amount ranges from about 0.01 mg/kg of body weight to about 100 mg/kg of body weight of a Compound of the present invention; in another embodiment, about 0.02 mg/kg of body weight to about 50 mg/kg of body weight; and in another embodiment, about 0.025 mg/kg of body weight to about 20 mg/kg of body weight.

In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated.

The effective dosage amounts described herein refer to total amounts administered; that is, if more than one Compound of the present invention, or a pharmaceutically acceptable derivative thereof, is administered, the effective dosage amounts correspond to the total amount administered.

The Compounds of the present invention, or a pharmaceutically acceptable derivative thereof, can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise administering to the animal being administered a Compound of the present invention, or a pharmaceutically acceptable derivative thereof (i.e., a first therapeutic agent) a second therapeutic agent. In one embodiment, the second therapeutic agent is administered in an effective amount. In one embodiment, the second therapeutic agent is administered in an effective amount.

An effective amount of the second therapeutic agent(s) will be known to those skilled the art depending on the agent. However, it is well within the skilled artisan's purview to determine the second therapeutic agent's optimal effective-amount range. A Compound of the present invention and the second therapeutic agent combined can act either additively or synergistically to treat the same Condition, or they can act independently of each other such that the Compound of the present invention treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., a synucleopathy such as RBD), the minimal effective amount of the Compound of the present invention will be less than its minimal effective amount would be where the second therapeutic agent is not administered. In this embodiment, the Compound of the present invention and the second therapeutic agent can act synergistically to treat or prevent a Condition. In one embodiment, a Compound of the present invention is administered concurrently with a second therapeutic agent as a single composition comprising an effective amount of a Compound of the present invention and an effective amount of the second therapeutic agent. Alternatively, a composition comprising an effective amount of a Compound of the present invention and a second composition comprising an effective amount of the second therapeutic agent are concurrently administered. In another embodiment, an effective amount of a Compound of the present invention is administered prior or subsequent to administration of an effective amount of the second therapeutic agent. In this embodiment, the Compound of the present invention is administered while the second therapeutic agent exerts its therapeutic effect, or the second therapeutic agent is administered while the Compound of the present invention exerts its therapeutic effect for treating or preventing a Condition.

The second therapeutic agent can be, but is not limited to, an opioid agonist, a non-opioid analgesic, a non-steroid anti-inflammatory agent, an antimigraine agent, a Cox-II inhibitor, an antiemetic, a β adrenergic blocker, an anticonvulsant, an antidepressant, a Ca2+ channel blocker, an anticancer agent, an agent for treating or preventing UI, an agent for treating or preventing an ulcer, an agent for treating or preventing IBD, an agent for treating or preventing IBS, an agent for treating addictive disorder, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating ALS, an agent for treating a cognitive disorder, an agent for treating vomiting, an agent for treating dyskinesia, an agent for treating depression, a pharmaceutically acceptable derivative thereof, or any mixture thereof.

Parkinson's Disease (PD)

In PD α-syn aggregates are found in neurons. Symptoms for PD are cardinal motor signs of bradykinesia, rigidity, tremor, and postural instability. The skilled person is aware of the diagnosis of PD. PD is described in detail for example in Postuma et al. (*Sleep Medicine* 21 (2016) 101-105), Berg et al. (Movement Disorders, Vol. 30, No. 12, 2015)

Dementia with Lewy Bodies (DLB)

In DLB aggregates of α-syn in neuronal somata (Lewy bodies) and processes (Lewy neurites) in typical distribution (neocortex and brain stem) can be found. The initial symptoms of DLB may comprise a reduction in cognitive performance with fluctuating episodes of poor and better cognitive performance. Deficits may involve the naming of objects, verbal fluency, visuospatial abilities, executive functions and trouble interpreting visual information. In particular, deficiencies in executive functions become apparent in tasks requiring planning, shifting between strategies, organizing, and self-monitoring. Memory impairment is usually not a common or predominant feature in DLB at the early stage of the disease. Furthermore, vivid, recurring or persistent visual hallucinations may frequently occur, as well as delusions, lack of initiative and motivation, depressed moods, and anxiety. At the time of diagnosis, akinetic-rigid movement disorder may already be present, but in most cases develops in the course of the illness. DLB is further described in McKeith et al. (Neurology 2005; 65; pp 1863-1872)

Magnetic resonance imaging (MRI) may reveal atrophy of the caudate nucleus, putamen, and thalamus. In contrast to Alzheimer's dementia, little atrophy is seen in the cortex, while the medial temporal lobe in particular is not atrophied. Basic diagnostic evaluation for DLB may include Neuropsychological tests, early visuospatial impairment (e.g. clock-drawing test, figure copying test), impaired speech (e.g. naming, verbal fluency), executive dysfunction, recommended Montreal Cognitive Assessment (MoCA) and Frontal Assessment Battery (FAB).

Functional brain imaging techniques can be used in the diagnosis of DLB. These technologies include single photon emission computed tomography (SPECT) and positron emission tomography (PET). In particular, $^{123}$I-N-ω-fluoropropyl-2β-carbomethoxy-3β-(4-iodophenyl)nortropan ($^{123}$I-FP-CIT)-SPECT can be used for dopamine transporter visualization, and PET with 2-Deoxy-2-[$^{18}$F]fluoroglucose ($^{18}$F-FDG) as a tracer for the assessment of regional cerebral glucose metabolism. Furthermore, PET with $^{18}$F-Dopa ($^{18}$F-Dopa-PET), $^{99}$Tc-hexamethylpropyleneamine oxime with SPECT ($^{99}$Tc-HMPAO-SPECT) and $^{123}$I-metaiodobenzylguanidine with SPECT ($^{123}$I-MIBG-SPECT) can be used for diagnostic evaluation. Moreover, PET in combination with other appropriate tracers can be used for demonstrating beta-amyloid deposition.

In DLB memory impairments are relatively mild and occur at a later stage (Mini Mental State Examination) and patients exhibit prominent visuo-spatial deficits (Clock Drawing Test), fluctuating cognitive performance; and mild atrophy of the medial temporal lobe including the hippocampus.

To distinguish between DLB and Parkinson's disease, the temporal sequence of symptom onset may be employed. If cognitive impairments precede movement disorder by at least one year, the diagnosis of DLB may be made. If motor disturbance occurs before or concomitantly with cognitive impairment, the condition may be classified as Parkinson's disease with dementia.

Multiple System Atrophy (MSA)

In MSA aggregates of α-syn can be found primarily in cytoplasm of oligodendrocytes (glial cytoplasmic inclusions) in a typical distribution (cerebellum, pons, and basal ganglia). MSA has two different subtypes, either with predominant cerebellar symptoms (MSA-C) or with predominant parkinsonism (MSA-P). MSA is further characterized in (Gilman S. et al., *Neurology* 2008; 71; pp 670-676).

In addition to motor impairment, vegetative symptoms may be a second component of MSA. In particular, urinary incontinence, erectile dysfunction, or orthostatic hypotension can occur.

Bradykinesia with rigidity, tremor, or postural instability may typical for MSA-P. A hypokinetic-rigid parkinsonian syndrome can be present in MSA-P, but in contrast to PD its presentation tends to be more symmetrical and less responsive to levodopa. Typical symptom of MSA is an irregular, higher-frequency postural tremor.

In MSA-C gait ataxia with cerebellar dysarthria, limb ataxia, or cerebellar oculomotor dysfunction can occur. The most common symptom is gait ataxia with wide-based movements. Furthermore, ataxia of the limbs is common, as are cerebellar oculomotor impairments, scanning dysarthria, and intention tremor.

Some further symptoms are typical of MSA, which can occur in both predominance types MSA-P and MSA-C. Patients, especially in advanced stages of the MSA, may have dysarthria, inspirational stridor, and dysphagia. Extrapyramidal signs may be seen in patients with MSA, but may not be in PD patients. Focal dystonias and posture abnormalities (e.g. antecollis, Pisa syndrome, contractures of the hands/feet) may be also observed in MSA patients.

The diagnosis of MSA requires at least one symptom of vegetative dysfunction (orthostatic hypotension, urinary incontinence, erectile dysfunction) after the exclusion of symptomatic causes. Furthermore, sporadic progressive parkinsonian symptoms (in MSA-P) or ataxia (in MSA-C) and at least one further typical symptom or a characteristic imaging finding are needed. Atrophy in the putamen, the middle cerebellar peduncle, the pons, and the cerebellum are visible on MRI. Hypometabolism in the putamen, brain stem, or cerebellum can be visualized by $^{18}$FDG-PET or $^{99}$Tc-HMPAO-SPECT. Symmetric striatal dopaminergic denervation can be visualized by $^{123}$I-FP-CIT-SPECT or $^{18}$F-Dopa-PET. Symmetric postsynaptic and striatal degeneration can be visualized by $^{123}$I-Iodobenzamide-SPECT ($^{123}$I-IBZM-SPECT) or $^{18}$F-desmethoxyfallypride-PET ($^{18}$F-DMFP-PET).

The clinical progression of MSA may be measured by a well-validated clinical score, the MSA Rating Scale (UM-SARS, Wenning et al. Mov Disord. 2004 December; 19(12), pp 1391-402) The UMSARS is divided in four parts, i.e. (i) historical review, (ii) motor examination, autonomic examination (iii) and global disability scale (iv). Due to the rapid course of the disease clinically relevant disease modifying effect may be observed in relatively short observation periods in MSA.

Rapid Eye Movement Sleep Behavior Disorder (RBD)

RBD may be characterized by loss of normal skeletal muscle atonia during rapid eye movement (REM) sleep with prominent motor activity and dreaming. Three primary aspects of RBD are abnormal vocalizations, abnormal motor behavior, and altered dream mentation. RBD is for example characterized in detail in Iranzo et al. (Lancet Neurol 2016; 15, pp 405-19).

RBD may be divided in idiopathic RBD (iRBD) and secondary or symptomatic RBD. iRBD refers to RBD occurring in the absence of any other obvious associated neurologic disorder. Secondary or symptomatic RBD may refer to the combination of RBD with another neurologic disorder, such as narcolepsy or a neurodegenerative disease.

The vocalizations in RBD tend to be loud and shouting, screaming, and swearing are common. Infrequent limb jerks are common during sleep in individuals without RBD, but in those with RBD, the motor activity often begins with some repetitive jerking or movements, followed by more activity such as punching, flailing, running, jumping out of bed, etc.

For the diagnosis of RBD polysomnography (PSG) can be conducted. The PSG monitors many body functions including brain (EEG), eye movements (EOG), muscle activity or skeletal muscle activation (EMG) and heart rhythm (ECG) during sleep.

RBD can begin years or decades before the onset of cognitive and motor features of PD, DLB, MSA, and PAF.

T2 signal changes on magnetic resonance imaging (MRI) in patients with RBD can be found, suggesting that vascular changes in the brainstem could disrupt REM sleep networks and result in RBD.

(N)-(3-iodopropene-2-yl)-2betacarbomethoxy-3beta-(4-chlorophenyl) tropane labeled with iodine 123 ($^{123}$IPT)-SPECT, which reflects presynaptic dopaminergic transporter integrity, and (S)-2hydroxy-3iodo-6-methoxy-([1-ethyl-2-pyrrolidinyl]methyl)benzamide labeled with iodine 123 ($^{123}$IBZM)-SPECT, which reflects postsynaptic dopaminergic D2 receptor integrity, can be used to investigate dopaminergic parameters in patients with RBD. Patients with RBD have reduced striatal IPT uptake compared to controls.

iRBD can be investigated by using (99m)Tc-Ethylene Cysteinate Dimer (ECD)-SPECT. Increased perfusion in the pons and putamen bilaterally and in the right hippocampus, and decreased perfusion in frontal and temporoparietal cortices can be found in iRBD patients.

Furthermore, $^{123}$I-FP-CIT-SPECT can be performed to investigate patients with suspected RBD. RBD patients show reduced nigrostriatal uptake, suggesting that iRBD patients with olfactory impairment might represent a preclinical α-synucleinopathy.

Dihydrotetrabenazine (DTBZ) positron emission tomography (PET) can be used to investigate RBD patients. Striatal binding of DTBZ was reduced in the iRBD subjects compared to controls, suggesting reduced dopaminergic substantia nigra neuron number. It can be concluded that this reduction is consistent with the hypothesis that RBD reflects an evolving degenerative parkinsonian disorder, and that RBD either reflects dysfunction of the PPN secondary to basal ganglia dysfunction, or primary dysfunction of the PPN or other brainstem structures that is temporally associated with basal ganglia dysfunction.

In one embodiment, RBD refers to conditions showing loss of normal skeletal muscle atonia during rapid eye movement (REM) sleep with prominent motor activity and dreaming, without Parkinson disease symptoms, such as bradykinesia, rigidity, tremor, and postural instability, in particular without tremor.

Pure Autonomic Failure (PAF)

PAF is a synucleinopathy with Lewy bodies and neuronal rarefaction in the intermediate-lateral tract of the medulla and in the sympathetic ganglia.

Diagnosis of PAF may be indicated in cases with clinical signs compatible with chronic sympathetic deficiency, without associated neurological signs. The diagnosis may confirmed with evidence of neurogenic orthostatic hypotension (falling>=20/10 mm Hg of arterial pressure when standing without reactive tachycardia). Ambulatory blood pressure monitoring can reveal a disappearance or reversal of the day/night rhythm. Specific tests for PAF (Ewing test, pupillary or sudoral function, analysis of heart rate and blood pressure variability, sympathetic microneurography and MIBG scintigraphy) may be carried out to for detailed diagnosis of PAF. Plasma levels of noradrenaline may be low at rest and do not increase on standing. The EMG and cerebral MRI/CT are normal. Examinations to identify an immunologic, deficiency, metabolic or toxic cause are negative.

Differential diagnoses include iatrogenic (including cardiovascular, urologic and psychotropic drugs) or curable (dehydration, venous insufficiency, anemia) causes of orthostatic hypotension, dopamine beta-hydroxylase deficiency, which may be ruled out by the presence of plasma noradrenaline in patients affected by orthostatic hypotension that is considered idiopathic, primary or secondary peripheral polyneuropathy (including diabetes, amyloidosis, renal dysfunction, Guillain-Barré syndrome (see these terms), those due to deficiency or paraneoplasic syndrome) or neurodegenerative disease dysautonomias (multiple system atrophy, Parkinson's disease; see these terms), which may be ruled out by normal neurological and paraclinical examinations in patients affected by PAF. The progression of PAF is slow, which distinguishes it from acute or sub-acute pandysautonomias.

Another aspect of the invention refers to a composition comprising one or more compounds as described herein and a pharmaceutically acceptable carrier.

Another aspect of the invention refers to vinpocetine or a pharmaceutically acceptable derivative thereof for use in the treatment of a synucleinopathy selected from the group consisting of MSA, PD, DLB, PAF, RBD, and inherited synucleinopathies caused by mutations or multiplications of the α-syn gene SNCA, or synucleinopathies caused by mutations in other genes including, but not limited to GBA, LRRK2 and PARK2. The specific embodiment MSA is selected from MSA with predominantly cerebellar symptoms (MSA-C) and MSA with predominantly parkinsonian symptoms (MSA-P), preferably MSA-C.

Another aspect of the invention refers to a composition comprising vinpocetine or a pharmaceutically acceptable derivative thereof and a pharmaceutically acceptable carrier for use according to the invention.

Correspondingly, the application relates to methods of treating a medical condition in a human or animal being by administering a modulator of PDE1A and/or PDE1C according to the invention. In particular, the application relates to methods of treating a synucleinopathies in a human or animal being by administering a modulator of PDE1A and/or PDE1C according to the invention.

Further, the application relates to modulator of PDE1A and/or PDE1C according to the invention in the manufacture of a medicament for the treatment of a medical condition. In particular, the application relates to modulator of PDE1A and/or PDE1C according to the invention in the manufacture of a medicament for the treatment of a synucleinopathy.

Experiments

Screening of FDA-Approved Drugs for Neuroprotective Efficacy Against α-Syn

The recently reported α-syn model (M. Hollerhage et al., Trifluoperazine rescues human dopaminergic cells from wild-type α-synuclein-induced toxicity, *Neurobiology of aging*. 35, 1700-1711 (2014)) was modified to be suitable for high-throughput screening. LUHMES cells were plated in culture flasks and transduced with adenoviral vectors to express wild type α-syn under the control of the CMV promoter one day after plating. One day after transduction, the cells were detached and re-plated into 384-well plates (FIG. 1A). Approximately 50% cell death was observed six days after transduction, using the percentage of cells showing propidium iodide incorporation of all cells visualized by nuclear staining with Hoechst 33342, as read-out. In this paradigm, 1,600 FDA-approved drugs were screened at concentrations of 3 µM and 10 µM, each in triplicates. A positive hit was defined by a Z-score above 2.5 after computing the median and median absolute deviation. A negative hit was defined by a Z-score below −3 (see FIG. 1B, C for exemplary results). The false-positive rate was 1.2%, defined as control wells, treated with DMSO, with a Z-score above 2.5. The false-negative rate, defined by wells without propidium iodide treatment showing up as negative hits, was 4.7%. This screening identified n=40 compounds to be protective at 3 µM and n=22 compounds at 10 µM in at least one out of three runs, n=8 compounds were protective in at least one run at both concentrations, n=53 compounds were protective in at least one of the six runs.

Dipyridamole Protected from α-Syn-Induced Toxicity

Dipyridamole was the most convincing hit, since it was protective in all six runs. The compound is an unspecific inhibitor of phosphodiesterases (PDEs). The protective effect of dipyridamole was validated using the quantification of LDH, released into the cell culture medium, as independent measure of cell death. Five µM of dipyridamole led to a reduction of the LDH level to 77.0±5.1% compared to α-syn overexpressing LUHMES cells with DMSO treatment (P<0.0001, FIG. 1D). Since dipyridamole does not pass the blood-brain barrier and may have unwanted effects due to its non-selective action on PDEs, it did not appear valuable for the treatment of PD. Hence, we investigated whether protection against α-syn mediated neurodegeneration could be achieved by more specific PDE inhibition.

LUHMES Cells Express Several PDEs

To narrow down which PDE is most relevant for the protective effect of dipyridamole, an expression analysis with Illumina HumanHT-12_V3 bead chips was performed in LUHMES cells ("Trifluoperazine rescues human dopaminergic cells from wild-type α-synuclein-induced toxicity." Hollerhage et al. Neurobiol Aging. 2014 July; 35(7):

1700-11) four days after transduction with α-syn expressing adenoviral vectors. PDE1A, PDE1C, PDE2A, PDE3B, PDE4C, PDE4D, PDE7A, PDE8A, PDE8B, and PDE9A were strongly expressed in LUHMES cells. PDE5A, PDE6B, PDE6G, and PDE11A had only very low expression levels, between 100 and 120 in arbitrary units. Other PDEs were not expressed (<100 in arbitrary units, FIG. 2A).

The PDE1 Inhibitor Vinpocetine Rescued LUHMES Cells from α-Syn-Induced Toxicity

We then tested specific inhibitors (D. H. Maurice et al., Advances in targeting cyclic nucleotide phosphodiesterases, *Nature reviews. Drug discovery.* 13, 290-314 (2014)) of the PDEs which were expressed in our cell model. Toxicity was determined by quantification of LDH released into the culture medium. The PDE1 inhibitor vinpocetine led to a significant protection in a dose dependent manner (FIG. 2B). Bay60-7550 (PDE2 inhibitor), Milrinone (PDE3 inhibitor), Rolipram (PDE4 inhibitor), Sildenafil (PDE5 inhibitor), BRL 50481 (PDE7 inhibitor), PF-4957325-00 (PDE 8 inhibitor), and Bay 73-6691 (PDE 9 inhibitor) did not have an effect on α-syn mediated toxicity (FIG. 2C-I).

To validate the data from the LDH measurement, we determined the number of vital 4',6-diamidino-2-phenylindole (DAPI)-stained nuclei in untransduced control cells and α-syn overexpressing cells treated without or with ascending concentrations of vinpocetine. The overexpression of α-syn led to a reduction of the cell number to 57.0±3.4% compared to untransduced controls (P<0.0001). After treatment with 20 μM vinpocetine, 85.1±4.1% of the cells survived (P<0.0001 vs. α-syn transduced cells with DMSO treatment, FIG. 3A). Consistently, treatment with 20 μM vinpocetine led to a significantly reduced activity of caspase 3 and 7 in LUHMES cells overexpressing α-syn, measured by quantification of the intracellular signal of CellEvent™, a fluorescence dye for activated caspase 3 and 7. The relative signal was 1.0±0.2 in untransduced cells and 74.8±5.7 in α-syn overexpressing cells treated with DMSO. After treatment with vinpocetine the signal was reduced to 25.6±2.1 (P<0.0001 vs. α-syn transduced cells with DMSO treatment, FIG. 3B, C).

Vinpocetine Reduced the Density of a 37 kDa α-Syn Band

In α-syn overexpressing LUHMES cells a 37 kDa α-syn immunoreactive Western blot band occurred, which was not present in untransduced LUHMES cells. Western blot analyses showed that this 37 kDa band most likely representing α-syn oligomers was reduced by treatment with vinpocetine in a dose dependent manner with 20 μM reducing the density of this band by 52.2±6.6% compared to α-syn overexpressing cells treated with DMSO (P<0.0001, FIG. 3D,E). Inversely, in α-syn overexpressing cells we observed an increase in the monomer α-syn band by treatment with vinpocetine. While DMSO treated α-syn overexpressing cells showed a 3.4±0.1-fold increased α-syn monomer band compared to untransduced controls, in α-syn overexpressing cells treated with 20 μM vinpocetine the α-syn monomer band was augmented to 5.1±0.4-fold (P=0.005, FIG. 3F). There was no change in other α-syn bands (FIG. 3G,H). Moreover, as previously observed the density of the 37 kDa band correlated with the LDH level in the cell culture medium ($r^2$=0.99, P=0.0002, FIG. I) and inversely correlated with the number of vital cells ($r^2$=0.96, P=0.004, FIG. 3J), indicating a direct causative role of this band in α-syn toxicity.

RNA Interference Confirmed that PDE1A was the Relevant Target of Vinpocetine

In order to confirm the mode of action of vinpocetine we performed a number of experiments. Since vinpocetine is also an inhibitor of sodium channels (M. Sitges, E. Galván, V. Nekrassov, Vinpocetine blockade of sodium channels inhibits the rise in sodium and calcium induced by 4-aminopyridine in synaptosomes, *Neurochemistry international.* 46, 533-540 (2005)) and L-type calcium channels (M. Sitges, A. Guarneros, V. Nekrassov, Effects of carbamazepine, phenytoin, valproic acid, oxcarbazepine, lamotrigine, topiramate and vinpocetine on the presynaptic Ca2+ channel-mediated release of [3H]glutamate: comparison with the Na+ channel-mediated release, *Neuropharmacology.* 53, 854-862 (2007)), we investigated whether inhibition of these channels was relevant for the protective effect. Therefore, LUHMES cells overexpressing α-syn were treated with the sodium channel blocker tetrodotoxin and the calcium channel blocker isradipine. Both compounds did not affect the α-syn mediated toxicity, proving that cation channel blockage was not relevant to reduce α-syn toxicity (FIG. 4A,B). PDE1, however can degrade cyclic adenosine monophosphate (cAMP) as well as cyclic guanosine monophosphate (cGMP). Hence, we investigated whether the observed effect of the PDE1 inhibitor vinpocetine was cAMP or cGMP-dependent. Therefore, we treated α-syn overexpressing LUHMES cells with forskolin, an adenylate cyclase stimulator (de Souza, N J, A. N. Dohadwalla, J. Reden, Forskolin: a labdane diterpenoid with antihypertensive, positive inotropic, platelet aggregation inhibitory, and adenylate cyclase activating properties, *Medicinal research reviews.* 3, 201-219 (1983).) and BAY41-2272 a guanylate cyclase stimulator (J. P. Stasch et al., NO-independent regulatory site on soluble guanylate cyclase, *Nature.* 410, 212-215 (2001)). The treatment of LUHMES cells with 10 μM forskolin had no influence on α-syn mediated toxicity. However, treatment of α-syn overexpressing LUHMES cells with 1 μM BAY41-2272 reduced the relative LDH release to 56.2±7.8% compared to α-syn overexpressing control cells (P=0.0001, FIG. 4C). This suggests that the protective effect observed after PDE1 inhibition was rather cGMP than cAMP-dependent. Furthermore, we performed knockdown experiment with siRNAs against different subtypes of PDE1. To this end, we treated α-syn overexpressing LUHMES cells with siRNAs against different PDE1 subtypes. While treatment with the siRNA against PDE1B did not reduce toxicity significantly, treatment with siRNAs against PDE1A and PDE1C significantly reduced toxicity of α-syn (FIG. 4D).

Recombinant Adeno-Associated Viral Vector-Mediated Overexpression of α-Syn Led to Nigral Neurodegeneration To investigate the neurotoxicity of α-syn in vivo, recombinant adeno-associated viral (rAAV) vectors were stereotactically injected into the substantia nigra of 11 weeks old mice to overexpress human wild type α-syn (rAAV-α-syn; FIG. 5A). The injection of rAAV vectors expressing luciferase (rAAV-luc) or injections with NaCl were used as controls for the toxicity of viral-mediated protein overexpression or the injection procedure itself. The treatment started one week after the intranigral injections. Therefore, the mice of each injection group (NaCl, rAAV-luc, and rAAV-α-syn) were randomized to be treated by daily intraperitoneal injections with 25 mg vinpocetine in solvent or the corresponding volume of solvent alone (FIG. 5B). All animals survived the injection procedure and treatment period. A subgroup of animals were not treated and sacrificed three weeks after injection to determine the transduction rate for rAAV-α-syn and rAAV-luc (each n=3).

The transduction rate with rAAV-α-syn was 91.7±0.6%, quantified by the percentage of dopaminergic cells which showed α-syn immunoreactivity. The transduction rate with rAAV-luc was 93.4±1.6%, respectively. There was no significant difference in the transduction rates between the two rAAVs.

To quantify the extent of neurodegeneration induced by rAAV mediated overexpression of α-syn, tyrosine-hydroxylase (TH) stainings of the substantia nigra and the striatum were performed. The number of TH$^+$ cells was determined by stereological counting. In the group of NaCl injected mice with solvent treatment, there was no significant difference in the number of TH$^+$ neurons between the injected (4108±54 cells) and the non-injected side (4168±92 cells, P=0.99, FIG. 5C, upper panel and FIG. 5D, blank columns). In mice transduced with rAAV-luc, the number of TH$^+$ neurons on the injected side was not significantly reduced (3806±182 cells on the injected side vs 4063±173 cells on the non-injected side, P=0.78 FIG. 5C, middle panel and FIG. 5D). α-syn overexpression, however, led to a decrease of TH$^+$ cells in the SN from 4087±130 on the non-injected side to 2915±79 on the injected side (P<0.0001, FIG. 5C, lower panel and FIG. 5D), which corresponded to an average decrease by 28.1±2.7% (range: 19.1 to 42.5%) compared to the non-injected side of the same animal. These results demonstrate that rAAV mediated overexpression of α-syn led to marked nigral neurodegeneration after 10 weeks.

Vinpocetine Treatment Rescued from α-Syn Mediated Neurodegeneration In Vivo

To determine the efficacy of vinpocetine in vivo, the number of TH$^+$ cells in the substantia nigra was determined in mice treated with daily injections of 25 mg/kg vinpocetine in solvent or the corresponding amount of solvent alone.

In the NaCl and rAAV-luc injection groups, there was no difference in the number of TH$^+$ neurons in the substantia nigra between mice treated with solvent or vinpocetine (FIG. 5E, upper and middle panel, FIG. 5F).

Remarkably, on the injection side of mice injected with rAAV-α-syn, there was a huge difference in the number of TH$^+$ cells in the substantia nigra between mice, which were treated with solvent and those, which were treated with vinpocetine (compare FIG. 5C, lower panel, circled area and FIG. 5E, lower panel, circled area). As described above in solvent treated mice the number of TH$^+$ neurons in the substantia nigra on the rAAV-α-syn injection side was reduced to 2915±79 (FIG. 5D, right side, dark grey column). In vinpocetine treated mice, however, the number of TH$^+$ cells on the α-syn injection side was 3870±141 (P<0.0001, FIG. 5F, right side, dark grey column). Moreover, there was no difference in the cell numbers on the injection side of NaCl (3984±160, P=0.99), rAAV-luc (3860±138, P=0.99), or rAAV-α-syn injected mice (3870±14, P=0.99) (FIG. 5F, right panel) injected mice.

Adeno-Associated Virus Injection did not Induce Microglial Activation

To determine, whether injection of rAAV induced an inflammatory reaction, a staining with an antibody against the microglial marker ibal was performed and the optical density of the ibal-immunoreactivity was measured. However, we did not observe any differences in the ibal-immunoreactivity in mice due to overexpression of α-syn or luciferase, nor any differences between the injection side and the non-injected side in any of the animal groups, nor any differences between vinpocetine and solvent treatment (data not shown). Thus, an inflammatory response due to overexpression of α-syn or treatment was not detectable.

The application also comprises the following embodiments:

1. A compound for use as a medicament, wherein the compound is a PDE1A modulator and/or a PDE1C modulator.
2. A compound for use in the prevention or the treatment of a medical condition, wherein the compound is a PDE1A modulator.
3. The compound for use according to item 1 or 2, wherein the PDE1A is a human PDE1A.
4. The compound for use according to any one of items 1 to 3, wherein the compound is a selective PDE1A modulator.
5. The compound for use according to any one of items 1 to 4, wherein the compound is a PDE1A inhibitor.
6. A compound for use in the prevention or the treatment of a medical condition, wherein the compound is a PDE1C modulator.
7. The compound for use according to item 1 or 6, wherein the PDE1C is a human PDE1C.
8. The compound for use according to any one of items 1, 6 or 7, wherein the compound is a selective PDE1C modulator.
9. The compound for use according to any one of items 1 or 6 to 8, wherein the compound is a PDE1C inhibitor.
10. A compound for use according to any one of items 1 to 9, wherein the compound is represented by the following formula (I)

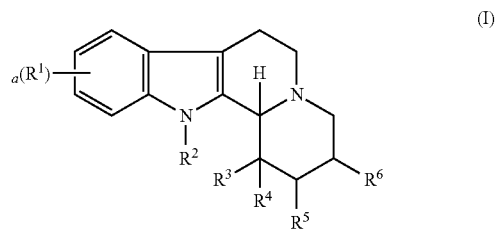

wherein
R$^1$ is selected from the group consisting of —H and halo,
a is 0, 1, 2, or 3, and preferably 0 or 1
R$^2$ is selected from the group consisting of —H and —(C$_1$-C$_6$)alkyl,
R$^3$ and R$^4$ are independently selected from the group consisting of —H, —OH, —(C$_1$-C$_6$)alkyl, and —(C$_1$-C$_6$)-hydroxyalkyl, or
R$^3$ and R$^4$ taken together are =O, or
R$^2$ and R$^3$ together with the nitrogen atom and carbon atom they are attached to form a 6-membered heterocyclic ring which is optionally substituted,
R$^5$ and R$^6$ are independently selected from the group consisting of —H and —(C$_1$-C$_6$)alkyl, or
R$^5$ and R$^6$ taken together form a carbon-carbon bond,
or a pharmaceutically acceptable derivative thereof,
wherein the alkyl and hydroxyalkyl groups are optionally substituted
and wherein the compound is not vinpocetine.
11. The compound for use according to item 10, wherein the 6-membered heterocyclic ring is optionally substituted with 1, 2, or 3 substituents selected from the group consisting of —COOR$^7$, —OH and —(C$_1$-C$_6$)alkyl, wherein R$^7$ is selected from the group consisting of —H, —(C$_1$-C$_{12}$)alkyl, —(C$_2$-C$_{12}$)alkenyl, —(C$_2$-C$_{12}$)alkynyl, —(C$_1$-C$_{12}$)alkyl-ONO$_2$, —(C$_2$-C$_{12}$)alkenyl- ONO$_2$, —(C$_2$-C$_{12}$)alkynyl-ONO$_2$, (6 to 14 membered) aryl, (5 to 10 membered)heteroaryl, trimethoxyphenyl, —(C$_1$-C$_6$)alkyl-(6 to 14 membered)aryl and —(C$_1$-C$_6$)alkyl-(5-10 membered)heteroaryl, wherein the alkyl, alkenyl, alkynyl, aryl and heteroaryl groups are optionally substituted.

12. The compound for use according to item 10 or 11, wherein the compound is represented by the following formula (II)

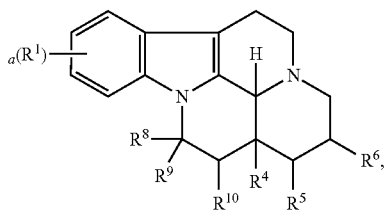

(II)

wherein
R$^1$ is selected from the group consisting of —H and halo,
a is 0, 1, 2, or 3, and preferably 0 or 1
R$^8$ is COOR$^7$,
R$^9$ and R$^{10}$ are independently selected from the group consisting of —H, —OH and —(C$_1$-C$_6$)alkyl, or
R$^9$ and R$^{10}$ taken together form a carbon-carbon bond,
R$^4$ is selected from the group consisting of —H, —OH, —(C$_1$-C$_6$)alkyl, and —(C$_1$-C$_6$)-hydroxyalkyl,
R$^5$ and R$^6$ are independently selected from the group consisting of —H and —(C1-C46)alkyl, or
R$^5$ and R$^6$ taken together form a carbon-carbon bond,
R$^7$ is selected from the group consisting of —H, —(C$_1$-C$_{12}$)alkyl, —(C$_2$-C$_{12}$)alkenyl, —(C$_2$-C$_{12}$)alkynyl, —(C$_1$-C$_{12}$)alkyl-ONO$_2$, —(C$_2$-C$_{12}$)alkenyl-ONO$_2$, —(C$_2$-C$_{12}$)alkynyl-ONO$_2$, (6 to 14 membered)aryl, (6 to 14 membered)heteroaryl, trimethoxyphenyl, —(C$_1$-C$_6$)alkyl-(6 to 14 membered)aryl and —(C$_1$-C$_6$)alkyl-(6 to 14 membered)heteroaryl
or a pharmaceutically acceptable derivative thereof,
wherein the alkyl, alkenyl, alkynyl, aryl and heteroaryl groups are optionally substituted.

13. A compound for use according to any one of items 1 to 9, wherein the compound is represented by the following formula (III)

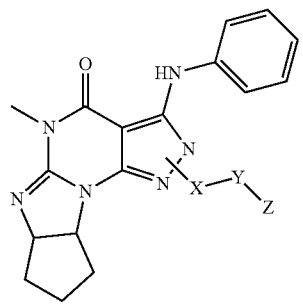

(III)

wherein
X is —(C$_1$-C$_6$)alkylene;
Y is a single bond, —(C$_2$-C$_{12}$)alkenylene, —(C$_2$-C$_{12}$)alkynylene, —(C$_6$-C$_{14}$)arylene or -(5-10 membered)heteroarylene;

Z is H, -(6 to 14 membered)aryl, -(5 to 10 membered) heteroaryl, halo, halo(C$_1$-C$_6$)alkyl, —C(O)—R$^1$, —N(R$^2$)(R$^3$), or —(C$_3$-C$_7$)cycloalkyl, wherein the —(C$_3$-C$_7$)cycloalkyl optionally comprises at least one heteroatom selected from a group consisting of N or O;
R$^1$ is —(C$_1$-C$_6$)alkyl, halo(C$_1$-C$_6$)alkyl;
R$^2$ and R$^3$ are independently selected from H or —(C$_1$-C$_6$)alkyl,
wherein X, Y and Z are independently and optionally substituted with halo,
or a pharmaceutically acceptable derivative thereof.

14. The compound for use according to item 13, wherein the compound is

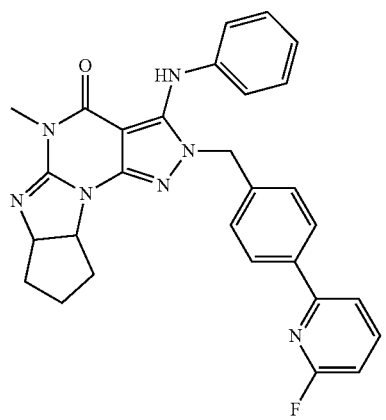

or a pharmaceutically acceptable derivative thereof.

15. The compound for use according to any one of items 1 to 9, wherein the compound is a nucleic acid.

16. The compound for use according to item 15, wherein the compound is RNA.

17. The compound for use according to item 16, wherein the RNA is single-stranded or double-stranded RNA.

18. The compound for use according to any one of items 16 or 17, wherein the RNA is selected from the group consisting of viral RNA, retroviral RNA, small interfering RNA (siRNA), antisense RNA, aptamers, microRNA (miRNA), double-stranded RNA (dsRNA), small hairpin RNA (shRNA), and Piwi-interacting RNA (piRNA).

19. The compound for use according to any one of items 16 to 18, wherein the RNA is selected from the group consisting of siRNA, antisense RNA, dsRNA, and shRNA.

20. The compound for use according to item 18, wherein the RNA is siRNA.

21. The compound for use according to any one of items 16 to 20, wherein the RNA comprises or consists of a nucleotide sequence which exhibits at least 50%, at least 60%, at least 70%, at least 80%, at least 85%, at least 90%, at least 95%, at least 96%, at least 97%, at least 98%, or at least 99% identity to the sequence according to SEQ ID NO:1 and/or SEQ ID NO: 3.

22. The compound for use according to any one of items 16 to 21, wherein the RNA comprises or consists of a nucleotide sequence of SEQ ID NO:1 and/or SEQ ID NO: 3.

23. The compound for use according to any one of items 15 to 22, wherein the nucleic acid is a synthetic nucleic acid.

24. The compound for use according to any one of items 15 to 23, wherein the nucleic acid is an isolated nucleic acid.

25. The compound for use according to any one of items 2 to 24, wherein the medical condition is a synucleinopathy.
26. The compound for use according to item 25, wherein the synucleinopathy is selected from Parkinson's disease (PD), Parkinson's disease with dementia (PDD), multiple system atrophy (MSA), dementia with Lewy bodies (DLB), pure autonomic failure (PAF), rapid eye movement sleep behavior disorder (RBD), or inherited synucleinopathies caused by mutations or multiplications of the alpha-synuclein gene SNCA, or synucleinopathies caused by mutations in other genes including, but not limited to GBA, LRRK2 and PARK2.
27. The compound for use according to item 26, wherein the multiple system atrophy (MSA) is selected from MSA with predominantly cerebellar symptoms (MSA-C) or MSA with predominantly parkinsonian symptoms (MSA-P).
28. An isolated vector encoding the RNA for use according to items 16 to 23.
29. A compound of Formula (I)

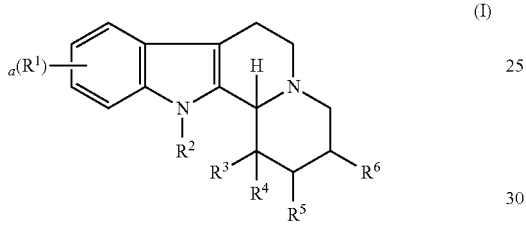

wherein
$R^1$ is selected from the group consisting of —H and halo,
a is 0, 1, 2, or 3, preferably a is 0 or 1;
$R^2$ is selected from the group consisting of —H and —($C_1$-$C_6$)alkyl,
$R^3$ and $R^4$ are independently selected from the group consisting of —H, —OH, —($C_1$-$C_6$)alkyl, and —($C_1$-$C_6$)-hydroxyalkyl, or
$R^3$ and $R^4$ taken together are =O, or
$R^2$ and $R^3$ together with the nitrogen atom and carbon atom they are attached to form a 6-membered heterocyclic ring which is optionally substituted,
$R^5$ and $R^6$ are independently selected from the group consisting of —H and —($C_1$-$C_6$)alkyl, or
$R^5$ and $R^6$ taken together form a carbon-carbon bond,
or a pharmaceutically acceptable derivative thereof,
wherein the alkyl and hydroxyalkyl groups are optionally substituted
and wherein the compound is not vinpocetine.
30. The compound according to item 29, wherein R2 and R3 together with the nitrogen atom and the carbon atom they are attached to for a 6-membered heterocyclic ring, the 6-membered heterocyclic ring may be substituted with 1, 2, or 3 substituents independently selected from the group consisting of —COOR$^7$, —OH and —($C_1$-$C_4$)alkyl;
wherein R$^7$ is selected from the group consisting of —H, —($C_1$-$C_{12}$)alkyl, —($C_2$-$C_{12}$)alkenyl, —($C_2$-$C_{12}$)alkynyl, —($C_1$-$C_{12}$)alkyl-ONO$_2$, —($C_2$-$C_{12}$)alkenyl-ONO$_2$, —($C_2$-$C_{12}$)alkynyl-ONO$_2$, -(6- to 14-membered)aryl, -(5- to 10-membered)heteroaryl, trimethoxyphenyl, —($C_1$-$C_6$)alkyl-(6- to 14-membered)aryl and —($C_1$-$C_6$)alkyl-(5- to 10-membered) heteroaryl;
wherein the alkyl, alkenyl, alkynyl, aryl and heteroaryl groups are optionally substituted.

31. The compound of formula (II)

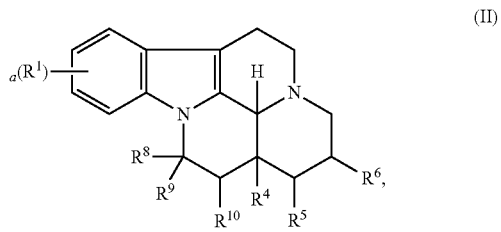

wherein
$R^1$ is selected from the group consisting of —H and halo,
a is 0, 1, 2, or 3, preferably a is 0 or 1;
$R^8$ is COOR$^7$,
$R^9$ and $R^{10}$ are independently selected from the group consisting of —H, —OH and —($C_1$-$C_6$)alkyl, or
$R^9$ and $R^{10}$ taken together form a carbon-carbon bond,
$R^4$ is selected from the group consisting of —H, —OH, —($C_1$-$C_6$)alkyl, and —($C_1$-$C_6$)-hydroxyalkyl,
$R^5$ and $R^6$ are independently selected from the group consisting of —H and —($C_1$-$C_{46}$)alkyl, or
$R^5$ and $R^6$ taken together form a carbon-carbon bond,
$R^7$ is selected from the group consisting of —H, —($C_1$-$C_{12}$)alkyl, —($C_2$-$C_{12}$)alkenyl, —($C_2$-$C_{12}$)alkynyl, —($C_1$-$C_{12}$)alkyl-ONO$_2$, —($C_2$-$C_{12}$)alkenyl-ONO$_2$, —($C_2$-$C_{12}$)alkynyl-ONO$_2$, (6 to 14 membered)aryl, (6 to 14 membered)heteroaryl, trimethoxyphenyl, —($C_1$-$C_6$)alkyl-(6 to 14 membered)aryl and —($C_1$-$C_6$)alkyl-(6 to 14 membered)heteroaryl
or a pharmaceutically acceptable derivative thereof,
wherein the alkyl, alkenyl, alkynyl, aryl and heteroaryl groups are optionally substituted A composition comprising one or more compounds of item 29 to 31 and a pharmaceutically acceptable carrier.
32. Vinpocetine or a pharmaceutically acceptable derivative thereof for use in the treatment of a synucleinopathy selected from the group consisting of multiple system atrophy (MSA), dementia with Lewy bodies (DLB), pure autonomic failure (PAF), rapid eye movement sleep behavior disorder (RBD), and inherited synucleinopathies caused by mutations or multiplications of the alpha-synuclein gene SNCA, or synucleinopathies caused by mutations in other genes including, but not limited to GBA, LRRK2 and PARK2.
33. Vinpocetine or a pharmaceutically acceptable derivative thereof for use in the treatment of a synucleinopathy according to item 33, wherein the multiple system atrophy (MSA) is selected from MSA with predominantly cerebellar symptoms (MSA-C) and MSA with predominantly parkinsonian symptoms (MSA-P).
34. Vinpocetine or a pharmaceutically acceptable derivative thereof for use in the treatment of a synucleinopathy according to item 34, wherein the synucleinopathy is MSA-C.
35. A composition comprising vinpocetine or a pharmaceutically acceptable derivative thereof and a pharmaceutically acceptable carrier for use according to any one of items 33 to 35.

The invention claimed is:

1. A method for treating a synucleinopathy in a human or non-human animal in need thereof, comprising:

administering a compound to said human or said non-human animal, wherein the compound is a PDE1A modulator and/or a PDE1C modulator, wherein the compound is represented by the following formula (I):

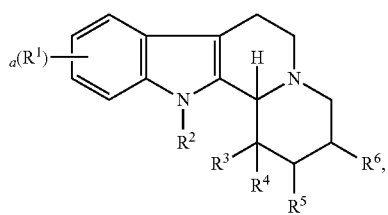

(I)

wherein $R^1$ is halo, a is 0, 1, 2, or 3, $R^2$ is selected from the group consisting of —H and —($C_1$-$C_6$)alkyl, $R^3$ and $R^4$ are independently selected from the group consisting of —H, —OH, —($C_1$-$C_6$)alkyl, and —($C_1$-$C_6$)-hydroxyalkyl, or $R^3$ and $R^4$ taken together are =O, or $R^2$ and $R^3$ together with the nitrogen atom and carbon atom they are attached to form a 6-membered heterocyclic ring which is optionally substituted, $R^5$ and $R^6$ are independently selected from the group consisting of —H and —($C_1$-$C_6$)alkyl, or $R^5$ and $R^6$ taken together form a carbon-carbon bond, or a pharmaceutically acceptable salt thereof, wherein the alkyl and hydroxyalkyl groups are optionally substituted, wherein the synucleinopathy is multiple system atrophy (MSA), dementia with Lewy bodies (DLB), pure autonomic failure (PAF), rapid eye movement sleep behavior disorder (RBD), or synucleinopathies caused by mutations in genes other than SNCA.

2. The method of claim 1, wherein the compound is a selective PDE1A modulator.

3. The method of claim 2, wherein the compound is a PDE1A inhibitor.

4. The method of claim 1, wherein the compound is a selective PDE1C modulator.

5. The method of claim 4, wherein the compound is a PDE1C inhibitor.

6. The method of claim 1, wherein the compound is represented by the following formula (II):

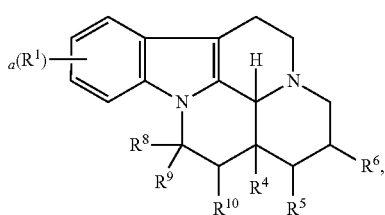

wherein
$R^1$ is halo,
a is 0, 1, 2, or 3,
$R^8$ is $COOR^7$,
$R^9$ and $R^{10}$ are independently selected from the group consisting of —H, —OH and —($C_1$-$C_6$)alkyl, or
$R^9$ and $R^{10}$ taken together form a carbon-carbon bond,
$R^4$ is selected from the group consisting of —H, —OH, —($C_1$-$C_6$)alkyl, and —($C_1$-$C_6$)-hydroxyalkyl,
$R^5$ and $R^6$ are independently selected from the group consisting of —H and —($C_1$-$C_{46}$)alkyl, or
$R^5$ and $R^6$ taken together form a carbon-carbon bond,
$R^7$ is selected from the group consisting of —H, —($C_1$-$C_{12}$)alkyl, ($C_2$-$C_{12}$)alkenyl, —($C_2$-$C_{12}$)alkynyl, —($C_1$-$C_{12}$)alkyl-$ONO_2$, —($C_2$-$C_{12}$)alkenyl-$ONO_2$, —($C_2$-$C_{12}$)alkynyl-$ONO_2$, (6 to 14 membered aryl, (6 to 14 membered)heteroaryl, trimethoxyphenyl, —($C_1$-$C_6$)alkyl-(6 to 14 membered)aryl and —($C_1$-$C_6$)alkyl-(6 to 14 membered)heteroaryl,
or a pharmaceutically acceptable salt thereof,
wherein the alkyl, alkenyl, alkynyl, aryl and heteroaryl groups are optionally substituted.

7. The method of c the synucleinopathy is MSA, wherein the MSA is MSA with predominantly cerebellar symptoms (MSA-C) or MSA with predominantly parkinsonian symptoms (MSA-P).

8. A method for treatment of a synucleinopathy in a human or a non-human in need thereof, comprising:
administering vinpocetine to said human or non-human animal,
wherein the synucleinopathy is selected from the group consisting of multiple system atrophy (MSA), dementia with Lewy bodies (DLB), pure autonomic failure (PAF), rapid eye movement sleep behavior disorder (RBD), and synucleinopathies caused by mutations in genes other than SNCA.

9. The method of claim 8, wherein the MSA is MSA with predominantly cerebellar symptoms (MSA-C) or MSA with predominantly parkinsonian symptoms (MSA-P).

10. The method of claim 1, wherein the synucleinopathy is multiple system atrophy (MSA), dementia with Lewy bodies (DLB), pure autonomic failure (PAF), or rapid eye movement sleep behavior disorder (RBD).

11. The method of claim 1, wherein the synucleinopathies is caused by mutations in a gene selected from the group consisting of GBA, LRRK2, and PARK2.

12. The method of claim 8, wherein the synucleinopathies is caused by mutations in a gene selected from the group consisting of GBA, LRRK2, and PARK2.

* * * * *